(12) United States Patent
Liu

(10) Patent No.: US 11,271,238 B2
(45) Date of Patent: Mar. 8, 2022

(54) APPLICATIONS OF LOW-COST, THERMAL AND ELECTROCHEMICALLY STABLE ORGANIC COMPOUNDS AS HIGH PERFORMANCE REDOX ACTIVE MATERIALS IN REDOX FLOW BATTERIES

(71) Applicant: Tianbiao Liu, Logan, UT (US)

(72) Inventor: Tianbiao Liu, Logan, UT (US)

(73) Assignee: Utah State University, Logan, UT (US)

(*) Notice: Subject to any disclaimer, the term of this patent is extended or adjusted under 35 U.S.C. 154(b) by 108 days.

(21) Appl. No.: 16/695,826

(22) Filed: Nov. 26, 2019

(65) Prior Publication Data
US 2020/0168910 A1 May 28, 2020

Related U.S. Application Data

(60) Provisional application No. 62/771,900, filed on Nov. 27, 2018.

(51) Int. Cl.
| | | |
|---|---|---|
| *H01M 8/18* | (2006.01) | |
| *H01M 4/60* | (2006.01) | |
| *H01M 4/36* | (2006.01) | |
| *C07D 513/04* | (2006.01) | |
| *H01M 8/023* | (2016.01) | |

(52) U.S. Cl.
CPC .......... *H01M 8/188* (2013.01); *C07D 513/04* (2013.01); *H01M 4/368* (2013.01); *H01M 4/60* (2013.01); *H01M 8/023* (2013.01); *H01M 2300/0002* (2013.01)

(58) Field of Classification Search
CPC ........ H01M 4/368; H01M 4/60; H01M 8/023; H01M 8/188; C07D 513/04

USPC ........................................... 429/108
See application file for complete search history.

(56) References Cited

U.S. PATENT DOCUMENTS

2010/0190956 A1* 7/2010 Wu ............... C07D 405/14
528/423
2018/0155321 A1* 6/2018 Kim ............... G02F 1/1503

FOREIGN PATENT DOCUMENTS

WO WO-2010099147 A1 * 9/2010 ........... G02F 1/1525
WO WO-2018021970 A1 * 2/2018 ......... C08G 73/0627

OTHER PUBLICATIONS

Beh et al., "A Neutral pH Aqueous Organic-Organometallic Redox Flow Battery with Extremely High Capacity Retention," ACS Energy Lett., 2017, 2(3):639-644.
Bird et al., "Electrochemistry of the viologens," Chem. Soc. Rev., 1981, 10(1):49-82.
Cong et al., "A Highly Concentrated Catholyte Enabled by a Low-Melting-Point Ferrocene Derivative," ACS Energy Lett., 2017, 2(4):869-875.
Ding et al., "Exploring Bio-inspired Quinone-Based Organic Redox Flow Batteries: A Combined Experimental and Computational Study," Chem, 2016, 1(5):790-801.

(Continued)

*Primary Examiner* — James M Erwin

(57) ABSTRACT

Described herein are redox active materials based on functionalization of 2,5-di(pyridine-4-yl)thiazolo-[5,4-d]thiazole (Py₂TTz). Also described herein are aqueous organic redox flow batteries that include a first redox active material and a second redox active material comprising a viologen compound or a salt thereof.

27 Claims, 14 Drawing Sheets

(56) References Cited

OTHER PUBLICATIONS

Er et al., "Computational design of molecules for an all-quinone redox flow battery," Chem. Sci., 2015, 6(2):885-893.
Gerhardt et al., "Anthraquinone Derivatives in Aqueous Flow Batteries," Adv. Energy Mater. 2017, 7(8):1601488.
Hu et al., "Boosting the energy efficiency and power performance of neutral aqueous organic redox flow batteries," J. Mater. Chem. A, 2017, 5(42):22137-22145.
Huang et al., "Liquid Catholyte Molecules for Nonaqueous Redox Flow Batteries," Adv. Energy Mater., 2015, 5(6):1401782.
Huang et al., "Next-Generation, High-Energy-Density Redox Flow Batteries," ChemPlusChem, 2015, 80(2):312-322.
Huskinson et al., "A metal-free organic-inorganic aqueous flow battery," Nature, 2014, 505(7482):195-198.
Janoschka et al., "An Aqueous Redox-Flow Battery with High Capacity and Power: The TEMPTMA/MV System," Angew. Chem. Int. Ed., 2016, 55(46):14427-14430.
Janoschka et al., "An aqueous, polymer-based redox-flow battery using non-corrosive, safe, and low-cost materials," Nature, 2015, 527(7576):78-81.
Leung et al., "Recent developments in organic redox flow batteries: A critical review," Journal of Power Sources, 2017, 360, 243-283.
Lin et al., "A redox-flow battery with an alloxazine-based organic electrolyte," Nat. Energy, 2016, 1, Article No. 16102.
Lin et al., "Alkaline quinone flow battery," Science, 2015, 349(6255):1529-1532.
Liu et al., "A Total Organic Aqueous Redox Flow Battery Employing a Low Cost and Sustainable Methyl Viologen Anolyte and 4-HO-TEMPO Catholyte," Adv. Energy Mater., 2016, 6(3):1501449.
Luo et al., "Unraveling pH dependent cycling stability of ferricyanide/ferrocyanide in redox flow batteries," Nano Energy, 2017, 42, 215-221.
Nanasawa et al., "Synthesis of Viologens with Extended $\pi$-Conjugation and Their Photochromic Behavior on Near-IR Absorption," J. Org.Chem., 2000, 65(2):593-595.
Nicholson, "Theory and Application of Cyclic Voltammetry for Measurement of Electrode Reaction Kinetics," Analytical Chemistry, 1965, 37(11):1351-1355.
Orita et al., "A biomimetic redox flow battery based on flavin mononucleotide," Nat. Commun., 2016, 7, Article No. 13230.
Porter III et al., "Synthesis and Characterization of a Highly Reducing Neutral "Extended Viologen" and the Isostructural Hydrocarbon 4,4'''-Di-n-octyl-p-quaterphenyl," J. Am. Chem. Soc., 2005, 127(47):16559-16566.
Reginato et al., "Photoactive Compounds Based on the Thiazolo[5,4-d]thiazole Core and Their Application in Organic and Hybrid Photovoltaics," Eur. J. Org. Chem., 2016, 2016(2):233-251.
Rueda-Garcia et al., "Hurdles to organic quinone flow cells. Electrode passivation by quinone reduction in acetonitrile Li electrolytes," Journal Power Sources, 2017, 350, 9-17.
Sevov et al., "Physical Organic Approach to Persistent, Cyclable, Low-Potential Electrolytes for Flow Battery Applications," J. Am Chem. Soc., 2017, 139(8):2924-2927.
Soloveichik, "Flow Batteries: Current Status and Trends," Chem. Rev., 2015, 115(20):11533-11558.
Son et al., "Quinone and its derivatives for energy harvesting and storage materials," J. Mater. Chem., A 2016, 4(29):11179-11202.
Takahashi et al., "Synthesis and characterization of new conjugation-extended viologens involving a central aromatic linking group," J. Chem. Soc. Chem. Commun., 1992, 8, 620-622.
Wang et al., "Recent Progress in Redox Flow Battery Research and Development," Adv. Funct. Mater., 2013, 23(8):970-986.
Wei et al., "Materials and Systems for Organic Redox Flow Batteries: Status and Challenges," ACS Energy Lett., 2017, 2(9):2187-2204.
Wei et al., "Radical Compatibility with Nonaqueous Electrolytes and Its Impact on an All-Organic Redox Flow Battery," Angew. Chem. Int. Ed., 2015, 54(30):8684-8687.
Wei et al., "Radical Compatibility with Nonaqueous Electrolytes and Its Impact on an All-Organic Redox Flow Battery," Angew. Chem., 2015, 127(30):8808-8811.
Wei et al., "TEMPO-based catholyte for high-energy density nonaqueous redox flow batteries," Adv. Mater., 2014, 26(45):7649-7653.
Winsberg et al., "Redox-Flow Batteries: From Metals to Organic Redox-Active Materials," Angew. Chem. Int. Ed., 2017, 56(3):686-711.
Woodward et al., "Thiazolothiazole Fluorophores Exhibiting Strong Fluorescence and Viologen-Like Reversible Electrochromism," J Am. Chem. Soc., 2017, 139(25):8467-8473.
Yang et al., "Electrochemical energy storage for green grid," Chem. Rev., 2011, 111(5):3577-3613.
Yang et al., "High-Performance Aqueous Organic Flow Battery with Quinone-Based Redox Couples at Both Electrodes," J. Electrochem. Soc., 2016, 163(7):A1442-A1449.
Zhu et al., "Unleashing the Power and Energy of LiFePO4-Based Redox Flow Lithium Battery with a Bifunctional Redox Mediator," J. Am. Chem. Soc., 2017, 139(18):6286-6289.

\* cited by examiner

APPLICATIONS OF LOW-COST, THERMAL AND ELECTROCHEMICALLY STABLE ORGANIC COMPOUNDS AS HIGH PERFORMANCE REDOX ACTIVE MATERIALS IN REDOX FLOW BATTERIES

CROSS-REFERENCE TO RELATED APPLICATIONS

This application claims priority to U.S. Patent Application No. 62/771,900, filed on Nov. 27, 2018, the contents of which are incorporated by reference herein in its entirety.

TECHNICAL FIELD

The present disclosure relates generally to redox active viologen-based materials and more particularly to aqueous organic redox flow batteries that include viologen-based redox active materials.

BACKGROUND

Redox flow batteries (RFBs) have been recognized as a possible renewable energy technology for large-scale energy storage. A redox flow battery generally includes a positive electrode electrolyte and a negative electrode electrolyte supplied to a battery element having a membrane interposed between a positive electrode and a negative electrode. An aqueous solution containing a metal ion having a valence which changes by oxidation-reduction is representatively used as the electrolytes. Traditional RFBs often suffer from drawbacks, such as expensive and resource limited redox active materials, corrosive and hazardous electrolytes, low current performance, and expensive system costs. As such, new technologies are needed make redox flow batteries viable for large-scale energy storage.

SUMMARY

In one aspect, disclosed are compounds of formula (I),

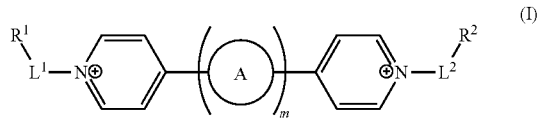

or a salt thereof, wherein:
m is 1, 2, or 3;
each A is independently selected from arylene or heteroarylene;
$L^1$ and $L^2$ are independently chosen from $C_1$-$C_{12}$ alkylene, $C_1$-$C_{12}$ alkenylene, $C_1$-$C_{12}$ alkynylene, —$C_1$-$C_4$ alkylene-(OCH$_2$CH$_2$)$_n$—, —$C_1$-$C_4$ alkylene-arylene-$C_1$-$C_4$ alkylene-, and —$C_1$-$C_4$ alkylene-arylene-(OCH$_2$CH$_2$)$_n$—;
n, at each occurrence, is independently 1, 2, or 3;
$R^1$ and $R^2$ are independently selected from the group consisting of —CH$_3$, —NO$_2$, —OR$^a$, —C(O)R$^b$, —C(O)OR$^c$, —S(O)$_q$, —PO$_3$, —S(O)$_q$R$^d$, —S(O)$_q$OR$^e$, —OP(O)(OR$^f$)$_2$, —OCH$_2$, —P(O)(OR$^g$)$_2$, —CHO, —(CR$^h_2$)$_q$CN, —N(R$^i$)$_q$, and —P(R$^j$)$_r$;
each R$^a$, R$^b$, R$^c$, R$^d$, R$^e$, R$^f$, R$^g$, R$^h$, R$^i$ and R$^j$ are independently selected from the group consisting of hydrogen, $C_1$-$C_4$ alkyl, cycloalkyl, heterocyclyl, aryl, heteroaryl, $C_1$-$C_4$ alkyl-N(R$^k$)$_w$, $C_1$-$C_4$ alkyl-S(O)$_w$, an oxygen protecting group, and a nitrogen protecting group;
R$^k$, at each occurrence, is independently selected from the group consisting of hydrogen, alkyl, cycloalkyl, heterocyclyl, aryl, heteroaryl, an oxygen protecting group, and a nitrogen protecting group;
q, at each occurrence, is independently 2 or 3;
r, at each occurrence, is independently 2, 3, or 4; and
w, at each occurrence, is independently 2 or 3;
wherein each aryl, heteroaryl, arylene, heteroarylene, cycloalkyl, and heterocyclyl is independently unsubstituted or substituted.

In another aspect, disclosed are redox flow batteries comprising a first redox active material and a second redox active material comprising the compounds described herein. In another aspect, disclosed are methods of storing and releasing energy comprising the redox flow batteries.

BRIEF DESCRIPTION OF THE DRAWINGS

FIG. 2A shows a plot of battery capacity versus cycling numbers of the [(NPr)$_2$TTz]Cl$_4$/N$^{Me}$-TEMPO AORFB at current densities from 40 mA cm$^{-2}$ to 100 mA cm$^{-2}$. FIG. 2B shows representative charge and discharge curves at current densities from 40 mA cm$^{-2}$ to 100 mA cm$^{-2}$ for the AORFB. FIG. 2C shows plots of average Coulombic efficiency (CE), energy efficiency (EE), and voltage efficiency (VE) at different operational current densities. FIG. 2D shows extended 300 cycle data of the AORFB showing charge capacity, discharge capacity, and Coulombic efficiency versus cycle number at 40 mA cm$^{-2}$ current density. Inset: Representative charge and discharge curves from the experiment. Conditions: anolyte: 0.1 m [(NPr)$_2$TTz]Cl$_4$ in 2 m NaCl; catholyte: 0.2 mN$^{Me}$-TEMPO in 2.0 m NaCl; AMV anion-exchange membrane, 25° C.

Figure 8:
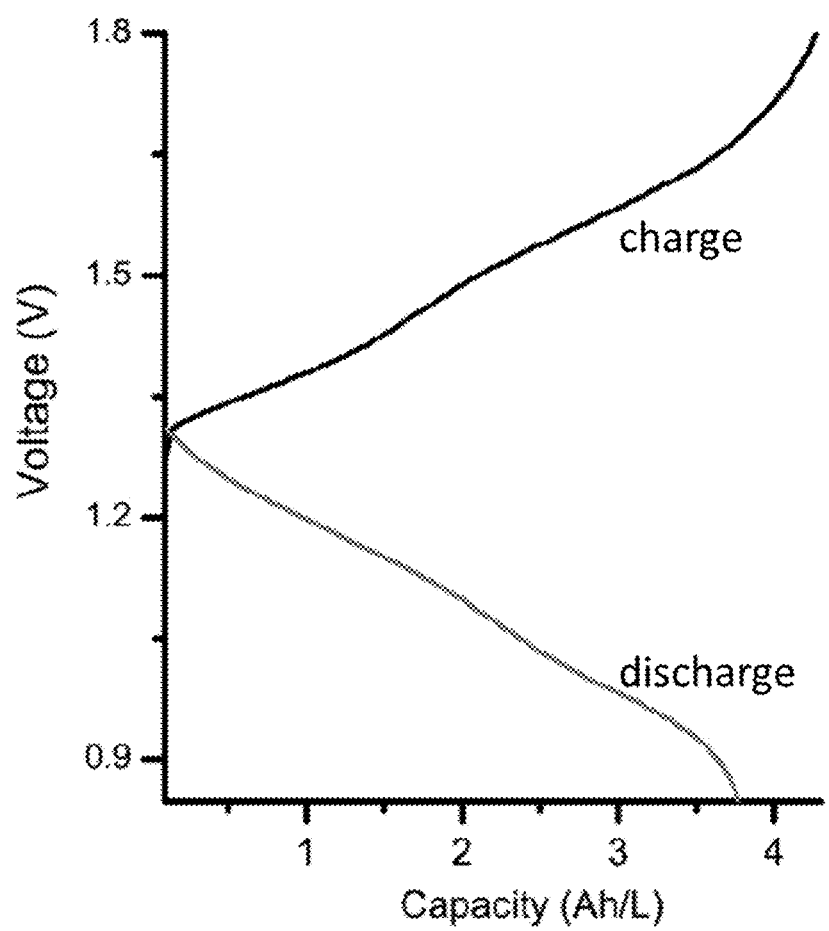

FIG. 8 shows a graph of charge and discharge curves of the [(NPr)$_2$TTz]Cl$_4$/N$^{Me}$-TEMPO AORFB at 40 mA/cm$^2$ operational current density.

Figure 9:
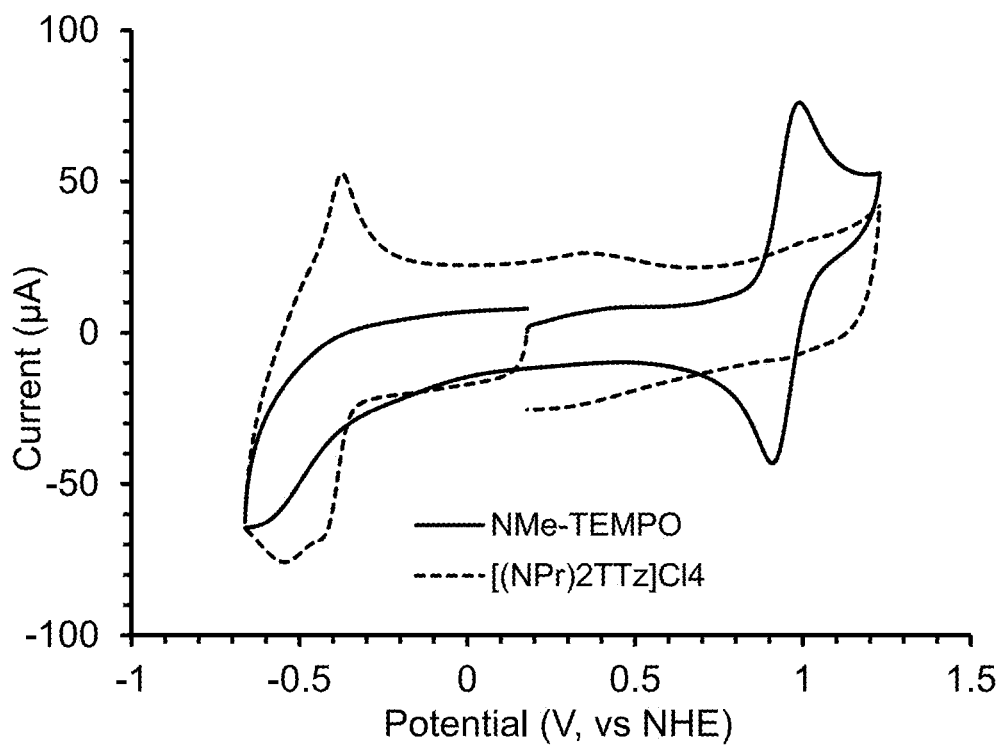

FIG. 9 shows the CV curves of the anolyte ([(NPr)$_2$TTz] Cl$_4$) and catholyte (N$^{Me}$-TEMPO) after 300 cycles of battery test.

Figure 10A:
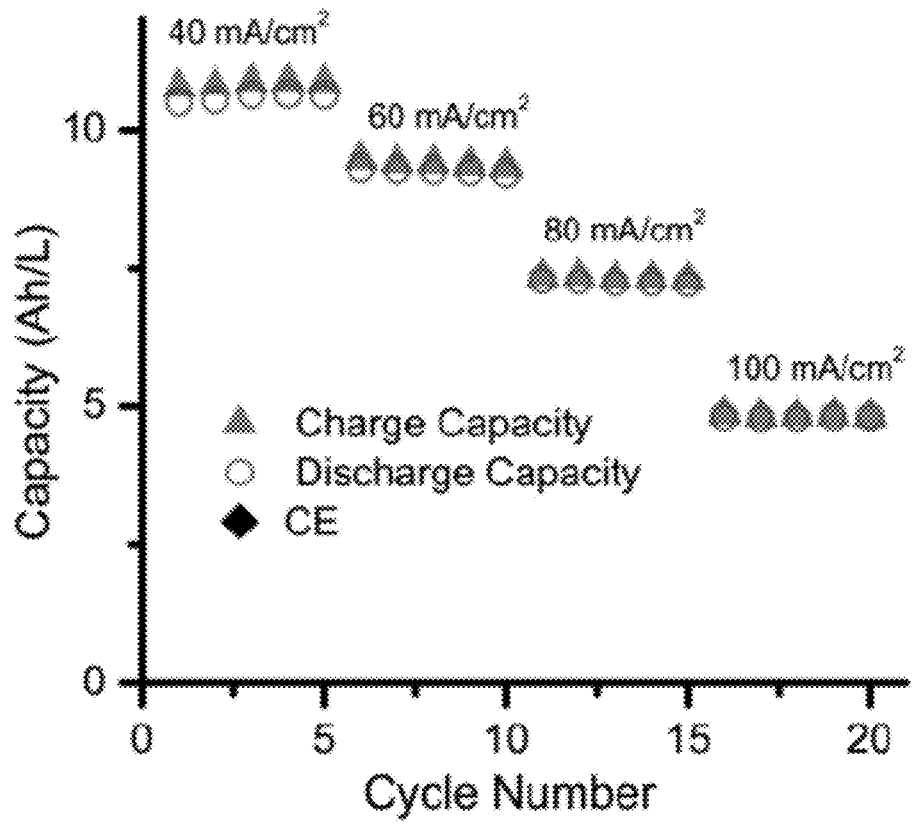
Figure 10B:
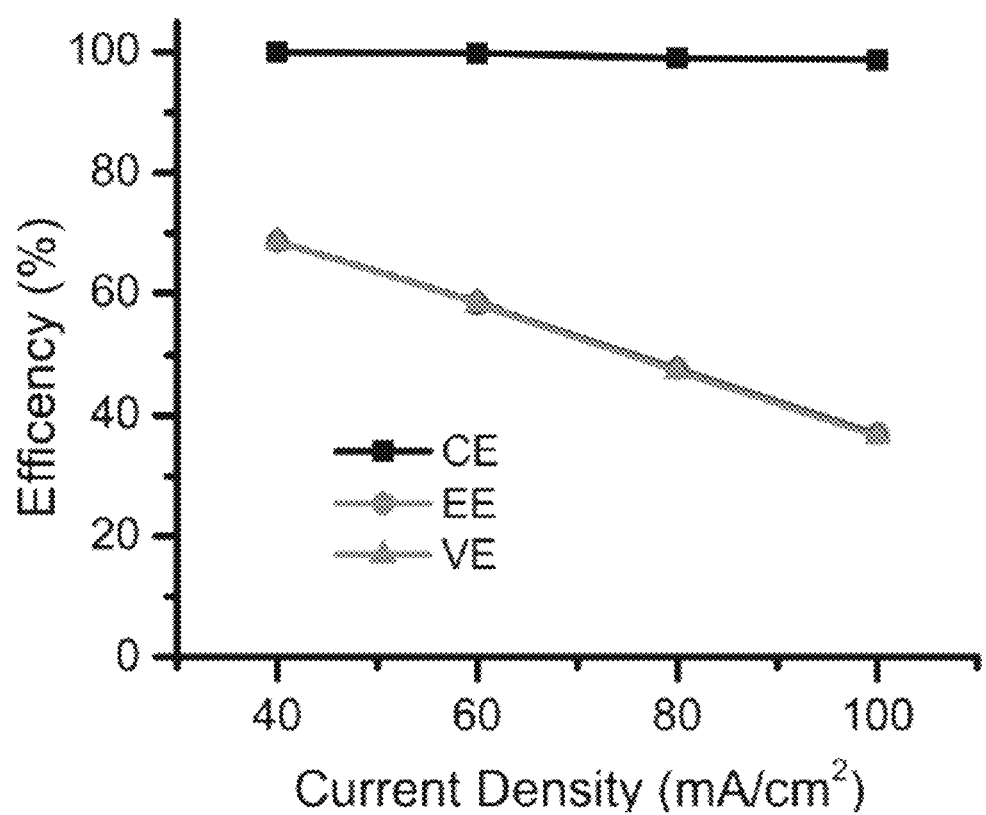
Figure 10C:
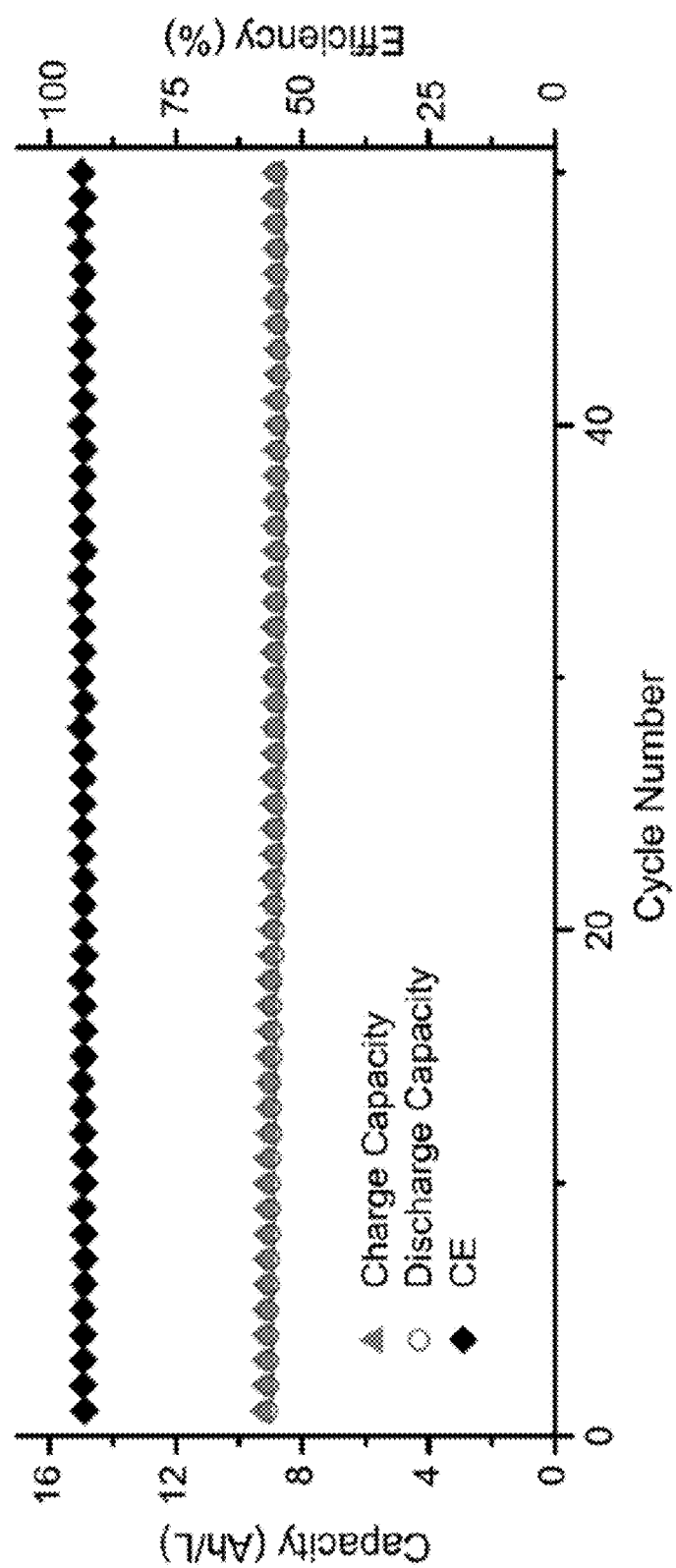

FIG. 10A, FIG. 10B, and FIG. 10C show plots of battery capacity, Coulombic efficiency, energy efficiency and voltage efficiency for a [(NPr)$_2$TTz]Cl$_4$/N$^{Me}$-TEMPO AORFB. FIG. 10A shows a plot of battery capacity versus cycling numbers of the [(NPr)$_2$TTz]Cl$_4$/N$^{Me}$-TEMPO AORFB at current densities from 40 mA/cm$^2$ to 100 mA/cm$^2$. FIG. 10B shows plots of average Coulombic efficiency (CE), energy efficiency (EE) and voltage efficiency (VE) at different operational current densities. FIG. 10C shows extended 50 cycle data of the AORFB showing charge capacity, discharge capacity, and Coulombic efficiency versus cycle number at 60 mA/cm$^2$ current density. Conditions: anolyte 0.25 M [(NPr)$_2$TTz]Cl$_4$ in 2 M NaCl; catholyte 0.5 M N$^{Me}$-TEMPO in 2.0 M NaCl; AMV anion-exchange membrane, 25° C.

DETAILED DESCRIPTION

With the advantages of decoupled energy and power, high current and power performance, non-flammable and low cost aqueous supporting electrolytes, as well as the tunable redox potentials of the organic active materials, aqueous organic redox flow batteries (AORFBs) have attracted increasing research and technology development for large scale and dispatchable storage (up to MW/MWh) of the intermittent renewable energy including solar and wind energy. In AORFBs, water-soluble organic redox active materials or compounds are applied as electrolyte materials. In the charge process, energy is stored by the reduction of anolyte and oxidation of catholyte; in the discharge process, the energy is outputted by the re-oxidation of anolyte and re-reduction of catholyte. Organic compounds have been used as electrolytes in AORFBs and non-aqueous organic redox flow batteries (NAORFBs). Water-soluble viologen (anolyte), ferrocene (catholyte), and TEMPO (catholyte) compounds demonstrated high performance neutral AORFBs. Among the reported organic compounds, only quinone or alloxazine based (anolyte) compounds are capable of storing two electrons in AORFBs, however, they have been applied in strong acidic or basic AORFBs. There is not a two-electron storage compound that is applied in a neutral aqueous system. In addition, very few total organic aqueous redox flow batteries with redox active organic electrolytes in both anode and cathode sides have been reported.

Disclosed herein are compounds that are redox active viologens designed through rational molecular engineering to achieve a new water-soluble two-electron storage anolyte compound. The compounds are based on functionalization of 2,5-di(pyridine-4-yl)thiazolo-[5,4-d]thiazole (Py$_2$TTz). Also disclosed are redox flow batteries comprising the compounds, and methods for using redox flow batteries comprising the compounds.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl," as used herein, means a straight or branched, saturated hydrocarbon chain containing from 1 to 10 carbon atoms. The term "lower alkyl" or "C$_1$-C$_6$-alkyl" means a straight or branched chain hydrocarbon containing from 1 to 6 carbon atoms. The term "C$_1$-C$_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene," as used herein, refers to a divalent group derived from a straight or branched, hydrocarbon chain containing at least one carbon-carbon double bond. Representative examples of alkenylene include, but are not limited to, —CH=CH—, —CH=CHCH$_2$—, and —CH$_2$CH=CHCH$_2$—.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH(CH$_3$)CH$_2$—, —CH$_2$CH$_2$CH$_2$CH$_2$—, —CH$_2$CH(CH$_3$)CH$_2$CH$_2$—, and —CH$_2$CH$_2$CH$_2$CH$_2$CH$_2$—.

The term "alkynylene," as used herein, refers to a group derived from a straight or branched, hydrocarbon chain containing at least one carbon-carbon triple bond. Representative examples of alkynylene include, but are not limited to, —C≡C—, —C≡CCH$_2$—, and —CH$_2$C≡CCH$_2$—.

The term "amino," as used herein, means —NR$_x$R$_y$, wherein R$_x$ and R$_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NR$_x$—, wherein R$_x$ may be hydrogen, alkyl, cycloalkyl, aryl, heteroaryl, heterocycle, alkenyl, or heteroalkyl.

The term "aryl," as used herein, refers to a phenyl group, a bicyclic fused ring system, or a tricyclic fused ring system. Fused ring systems are exemplified by a first aryl group fused to a cycloalkyl group, as defined herein, a phenyl group, a heteroaryl group, as defined herein, a second aryl group, or a heterocycle, as defined herein. Representative examples of aryl include, but are not limited to, indolyl, naphthyl, phenyl, benzodioxolyl, tetrahydroquinolinyl, anthracyl, and phenanthracyl.

The term "cycloalkyl," as used herein, refers to a carbocyclic ring system containing three to ten carbon atoms, zero heteroatoms and zero double bonds. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "halogen" or "halo," as used herein, means Cl, Br, I, or F.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic or tricyclic ring system. The aromatic monocyclic rings are five or six membered rings containing at least one heteroatom independently selected from the group consisting of N, O and S (e.g., 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a bicyclic heteroaryl ring fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-c]pyridinyl, naphthyridinyl, pyridoimidazolyl, thiazolo[5,4-b]pyridin-2-yl, thiazolo[5,4-d]pyrimidin-2-yl, thiazolo[5,4-d] thiazolyl, furo[3,2-b]furanyl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1³,⁷]decane), and oxa-adamantane (2-oxatricyclo[3.3.1.1³,⁷]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

In some instances, the number of carbon atoms in a hydrocarbyl substituent (e.g., alkyl or cycloalkyl) is indicated by the prefix "$C_x$-$C_y$—", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, cycloalkyl, or heterocyclyl group at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "≡" designates a single bond (—) or a double bond (=).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "active material" or "redox active material" refers to materials which undergo a change in oxidation state during operation of an electrochemical system, such as a flow battery. In certain embodiments, types of active materials comprise species dissolved in a liquid electrolyte. A type of redox active material may comprise a single species or may comprise multiple species.

The term "metallocene" as used herein, refers to a compound comprising at least one $\eta^3$ to $\eta^5$-cycloalkadienyl-type moiety, wherein $\eta^3$ to $\eta^5$-cycloalkadienyl moieties include cyclopentadienyl, indenyl, fluorenyl, and the like, including saturated or substituted derivatives or analogs of any of these. An example of a metallocene is ferrocene.

The term "nitrogen protecting group" as used herein refers to substituents that can be introduced to protect nitrogen-containing functional groups (e.g., —$NH_2$ or NHR) from undesired reactions. Exemplary nitrogen protecting groups include, but are not limited to, p-methoxyphenyl ("PMP"), benzyl, methyl, triphenylmethyl, pivaloyl, pyrrolidinylmethyl, t-butoxycarbonyl, silyl, acetyl, benzyloxycarbonyl (Cbz) and trimethylsilyethoxymethyl (SEM).

The term "oxygen protecting group" as used herein refers to substituents that can be introduced to protect oxygen-containing functional groups (e.g., —OH) from undesired reactions. Exemplary oxygen protecting groups include, but are not limited to, silyl ethers, methyl ethers, alkyl ethers, benzyl ethers, esters, benzoates, carbonates, and sulfonates.

The term "substituted" as used herein refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy (e.g., —OH), hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkyl sulfonyl, aryl sulfonyl, aminosulfonyl, sulfinyl, sulfonatyl (e.g., —$SO_3^-$, —$SO_3H$, etc.), —$PO_3^{-2}$, —$PO_3H^-$—COOH, ketone, amide, carbamate, and acyl.

The term "viologen" as used herein refers to a compound that includes a 4,4'-bypyridyl core structure.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed is a compound of formula (I):

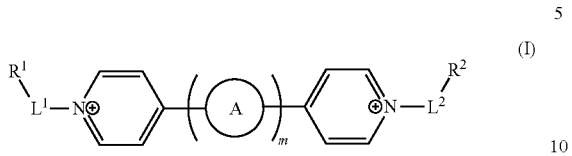
(I)

or a salt thereof, wherein:

m is 1, 2, or 3;

each A is independently selected from arylene or heteroarylene;

$L^1$ and $L^2$ are independently chosen from $C_1$-$C_{12}$ alkylene, $C_1$-$C_{12}$ alkenylene, $C_1$-$C_{12}$ alkynylene, —$C_1$-$C_4$ alkylene-(OCH$_2$CH$_2$)$_n$—, —$C_1$-$C_4$ alkylene-arylene-$C_1$-$C_4$ alkylene-, and —$C_1$-$C_4$ alkylene-arylene-(OCH$_2$CH$_2$)$_n$—;

n, at each occurrence, is independently 1, 2, or 3;

$R^1$ and $R^2$ are independently selected from the group consisting of —CH$_3$, —NO$_2$, —OR$^a$, —C(O)R$^b$, —C(O)OR$^c$, —S(O)$_q$, —PO$_3$, —S(O)$_q$R$^d$, —S(O)$_q$OR$^e$, —OP(O)(OR$^f$)$_2$, —OCH$_2$, —P(O)(OR$^g$)$_2$, —CHO, —(CR$^h{}_2$)$_q$CN, —N(R$^i$)$_q$, and —P(R$^j$)$_r$;

each $R^a$, $R^b$, $R^c$, $R^d$, $R^e$, $R^f$, $R^g$, $R^h$, $R^i$ and $R^j$ are independently selected from the group consisting of hydrogen, $C_1$-$C_4$ alkyl, cycloalkyl, heterocyclyl, aryl, heteroaryl, $C_1$-$C_4$ alkyl-N(R$^k$)$_w$, $C_1$-$C_4$ alkyl-S(O)$_w$, an oxygen protecting group, and a nitrogen protecting group;

$R^k$, at each occurrence, is independently selected from the group consisting of hydrogen, alkyl, cycloalkyl, heterocyclyl, aryl, heteroaryl, an oxygen protecting group, and a nitrogen protecting group;

q, at each occurrence, is independently 2 or 3;

r, at each occurrence, is independently 2, 3, or 4; and w, at each occurrence, is independently 2 or 3;

wherein each aryl, heteroaryl, arylene, heteroarylene, cycloalkyl, and heterocyclyl is independently unsubstituted or substituted.

In some embodiments, A is selected from the group consisting of:

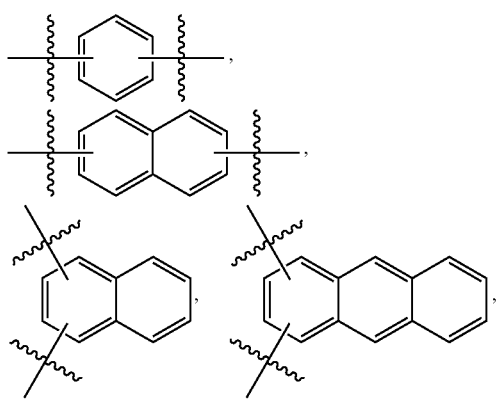

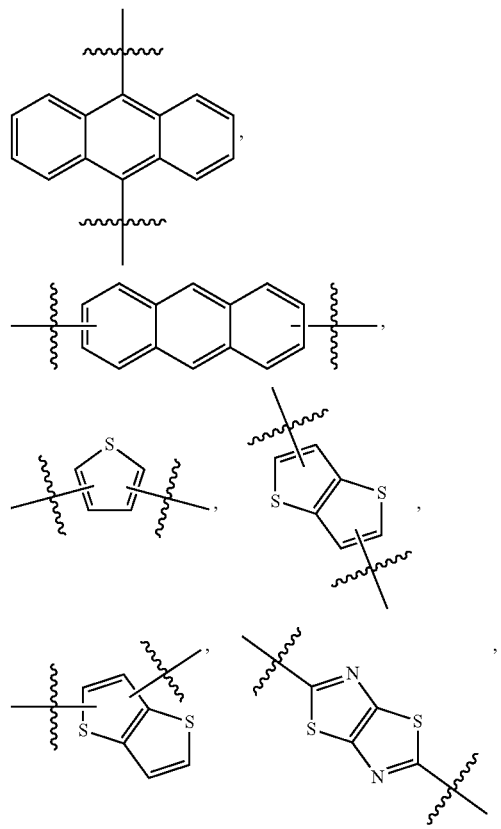

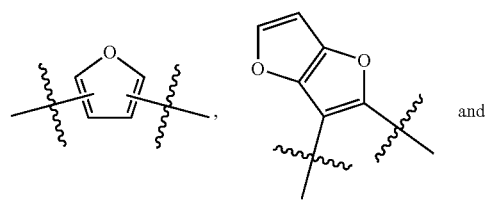 and

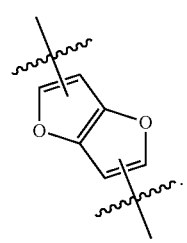

In some embodiments, A is

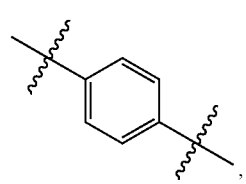

-continued

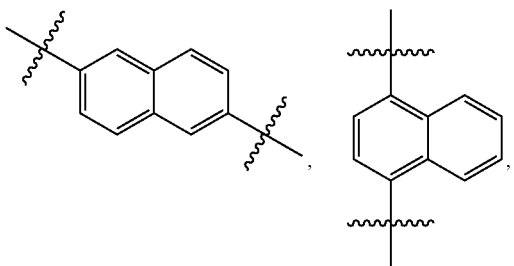

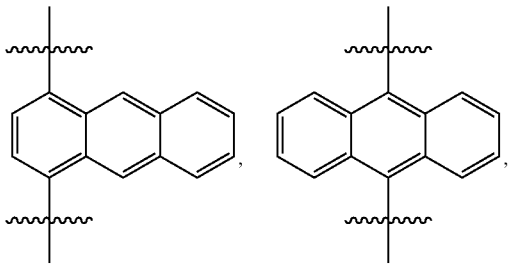

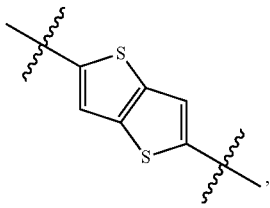

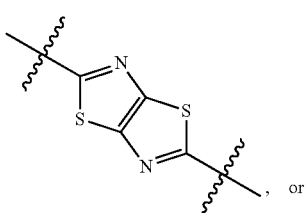

In some embodiments, A is

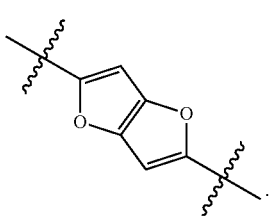

In some embodiments, m is 2 and A is a five-membered or six-membered arylene or heteroarylene. In certain embodiments, m is 2 and A is

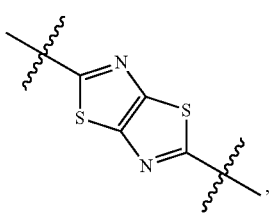 [SMILES: *c1nc2sc(*)nc2s1]

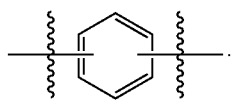

In some embodiments, $L^1$ and $L^2$ are independently $C_1$-$C_{12}$ alkylene. In some embodiments, $L^1$ and $L^2$ are independently $C_1$-$C_6$ alkylene. In some embodiments, $L^1$ and $L^2$ are $C_3$ alkylene.

In some embodiments, $L^1$ and $L^2$ are independently $C_1$-$C_{12}$ alkylene and A is

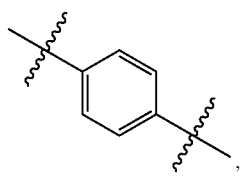

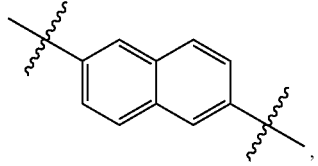 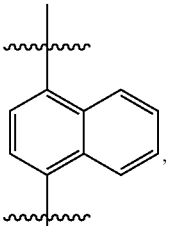

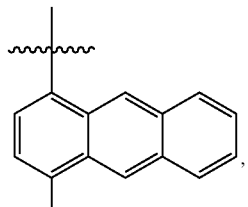

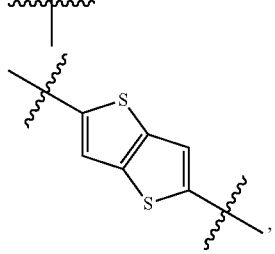

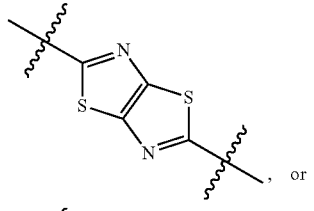, or

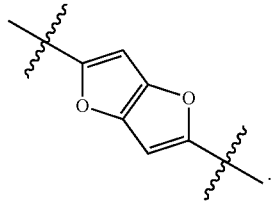 [SMILES: *c1nc2sc(*)nc2s1]

In some embodiments, $L^1$ and $L^2$ are independently $C_1$-$C_6$ alkylene and A is

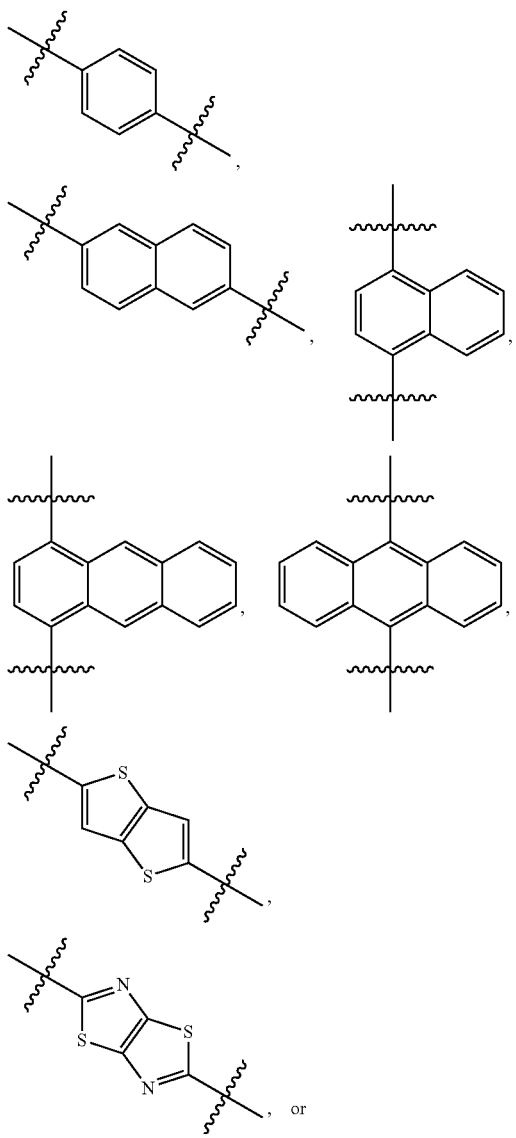

In some embodiments, $L^1$ and $L^2$ are $C_3$ alkylene and A is

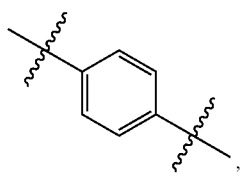

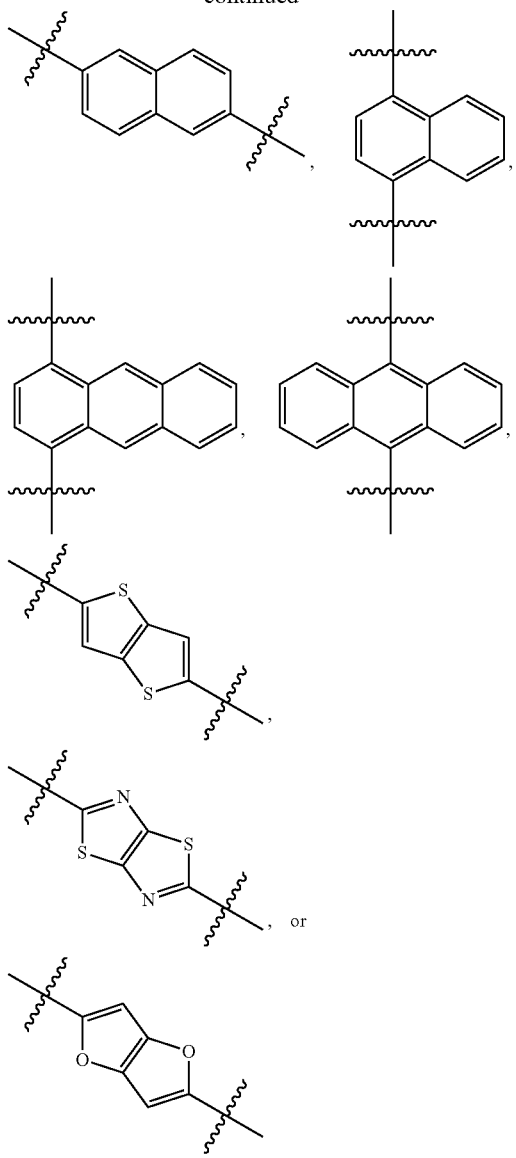

In some embodiments, $L^1$ and $L^2$ are $C_3$ alkylene and A is

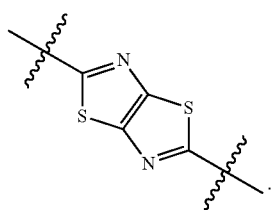 [SMILES: *c1nc2sc(*)nc2s1]

In some embodiments, $R^1$ and $R^2$ are independently selected from the group consisting of —S(O)$_q$, —PO$_3$, —S(O)$_q$R$^d$, and —N(R$^i$)$_q$ wherein R$^d$ and R$^i$ are independently selected from the group consisting of hydrogen, $C_1$-$C_4$ alkyl, cycloalkyl, heterocyclyl, aryl, heteroaryl, $C_1$-$C_4$ alkyl-N(R$^k$)$_w$, $C_1$-$C_4$ alkyl-S(O)$_w$, an oxygen protecting group, and a nitrogen protecting group and q is independently 2 or 3.

In some embodiments, each $R^a$, $R^b$, $R^c$, $R^d$, $R^e$, $R^f$, $R^g$, $R^h$, $R^i$ and $R^j$ are independently selected from hydrogen and $C_1$-$C_4$ alkyl.

In some embodiments, $R^1$ and $R^2$ are —$N(R^i)_q$. In some embodiments, $R^1$ and $R^2$ are $N(R^i)_q$ wherein $R^i$ is $C_1$-$C_4$ alkyl and q is 3. In certain embodiments, $R^1$ and $R^2$ are —$N(R^i)_q$ wherein $R^i$ is methyl and q is 3.

In some embodiments, $R^1$ and $R^2$ are independently selected from the group consisting of —$S(O)_q$, —$PO_3$, —$S(O)_qR^d$, and —$N(R^i)_q$, $L^1$ and $L^2$ are independently $C_1$-$C_{12}$ alkylene and A is

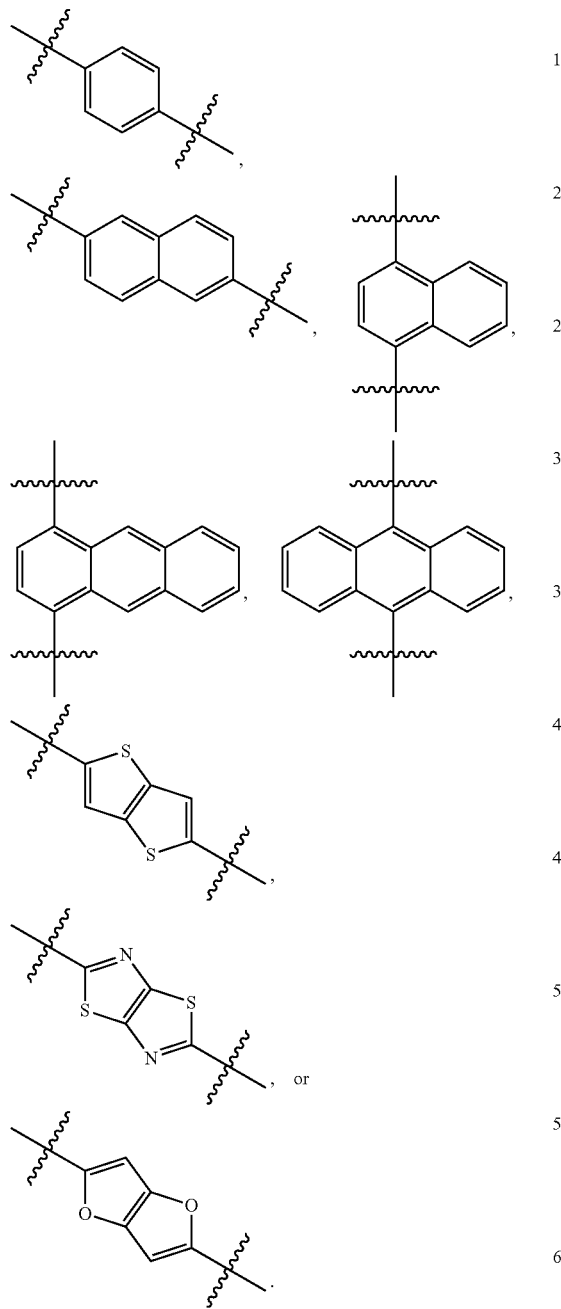

In some embodiments, $R^1$ and $R^2$ are independently selected from the group consisting of —$S(O)_q$, —$PO_3$, —$S(O)_qR^d$, and —$N(R^i)_q$, $L^1$ and $L^2$ are independently $C_1$-$C_6$ alkylene and A is

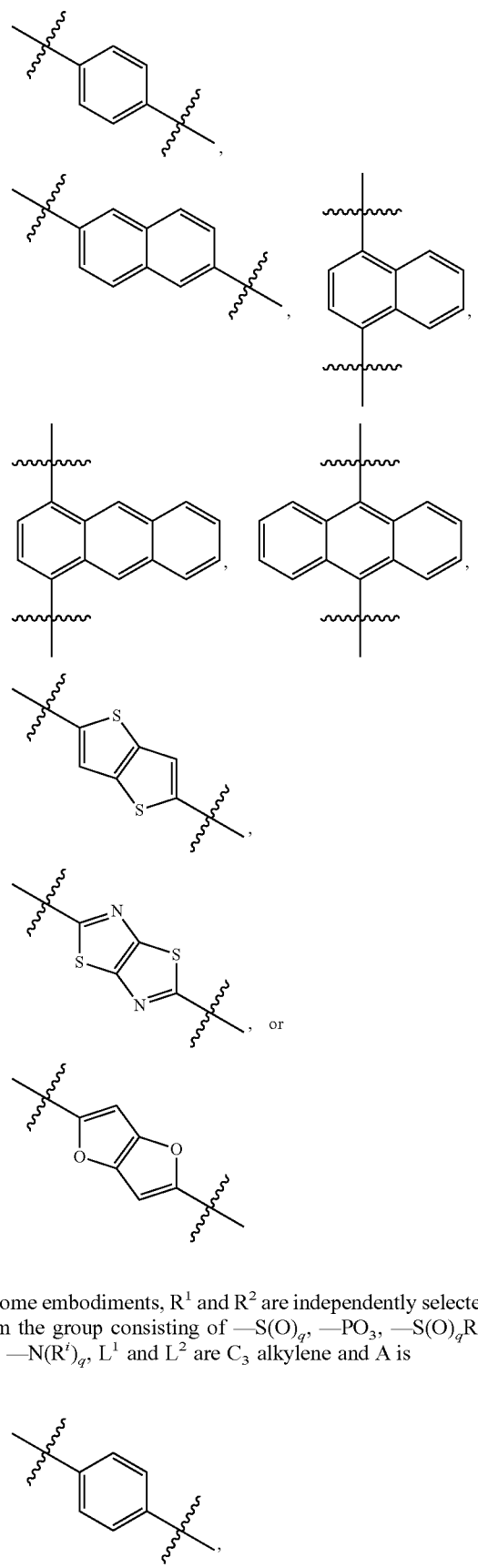

In some embodiments, $R^1$ and $R^2$ are independently selected from the group consisting of —$S(O)_q$, —$PO_3$, —$S(O)_qR^d$, and —$N(R^i)_q$, $L^1$ and $L^2$ are $C_3$ alkylene and A is

17

-continued

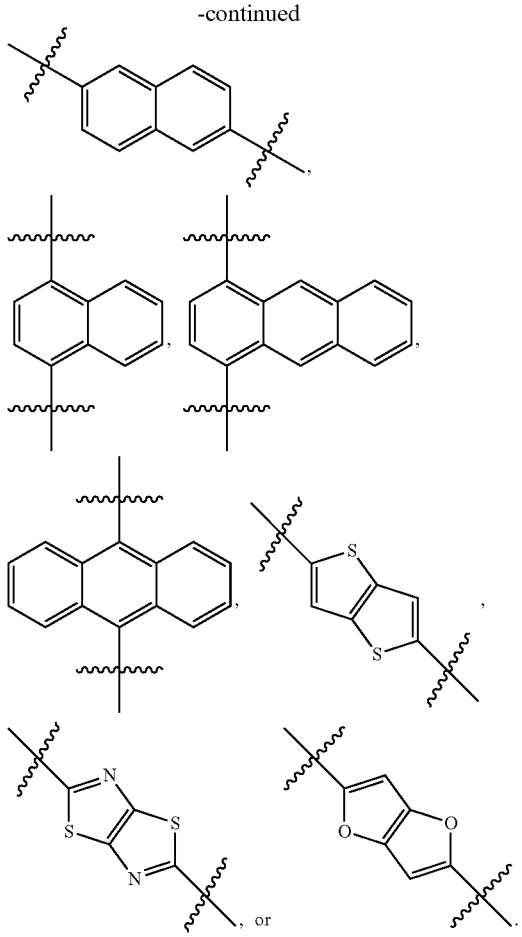

In some embodiments, $R^1$ and $R^2$ are $-N(R^i)_q$, $L^1$ and $L^2$ are $C_3$ alkylene and A is

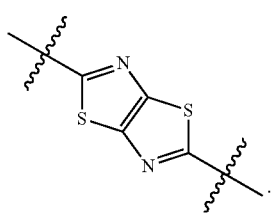 [SMILES: *c1nc2sc(*)nc2s1]

In certain embodiments, $R^1$ and $R^2$ are $-N(CH_3)_3$, $L^1$ and $L^2$ are $C_3$ alkylene and A is

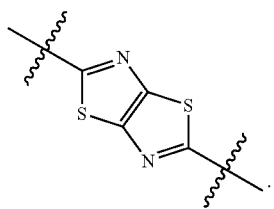

In some embodiments, the compound of formula (I) is a salt of fluoride, chloride, bromide, iodide, hydroxide, sulfate, carbonate, chlorate, perchlorate, phosphate, dihydrogen phosphate, hydrogen phosphate, nitrate, nitride, nitrile, dicyanamide, thiocyanate, bis(trifluoromethane)sulfonamide, hexafluorophosphate, tetrafluorophosphite, or a combination thereof. In certain embodiments, the compound of formula (I) is a salt of fluoride, chloride, bromide or iodide.

In some embodiments, the compound of formula (I) may have an overall neutral charge (e.g., where the substituents balance the positive charge of the bipyridyl-core structure, such as when $R^1$ and $R^2$ are $-SO_3^-$).

3. Aqueous Organic Redox Flow Batteries

Aqueous organic redox flow batteries (AORFBs) have potential for being affordable, and safe, and can have a high theoretical energy density. An aqueous organic redox flow battery may be thought of as a rechargeable battery with a continuous flow of one aqueous reactant past its negative, or low potential, electrode and a continuous flow of another aqueous reactant past its positive, or high-potential, electrode.

The disclosed aqueous organic redox flow batteries (AORFBs) include a first redox active material and a second redox active material comprising a viologen compound as disclosed herein or salt thereof.

The batteries may further include an aqueous electrolyte(s) (e.g., a first and second aqueous electrolyte), a separator, a first electrode, and a second electrode. The AORFB may balance electroneutrality through an ion exchange mechanism. Whether the AORFB operates through a cation or anion exchange can depend on the different redox active materials being used.

The batteries may also further include circulation loop(s) to pump the aqueous electrolyte(s). In certain embodiments, the AORFB includes a first circulation loop including a first storage tank containing the first aqueous electrolyte, piping for transporting the first aqueous electrolyte, a chamber in which the first electrode is in contact with the first aqueous electrolyte, and a pump to circulate the first aqueous electrolyte through the first circulation loop; a second circulation loop including a second storage tank containing the second aqueous electrolyte, piping for transporting the second aqueous electrolyte, a chamber in which the second electrode is in contact with the second aqueous electrolyte, and a pump to circulate the second aqueous electrolyte through the second circulation loop; and optionally control hardware and software.

The disclosed aqueous organic redox flow batteries may be both charged and discharged. In certain embodiments, during charge, the first redox active material present in a first aqueous electrolyte undergoes oxidation, and the second redox active material present in a second aqueous electrolyte undergoes reduction, whereas during discharge, the first redox active material present in the first aqueous electrolyte undergoes reduction, and the second redox active material present in the second aqueous electrolyte undergoes oxidation. In still other embodiments, the roles of the electrolytes are reversed, such that during charge the first redox active material present in the first aqueous electrolyte undergoes reduction, and the second redox active material present in the second aqueous electrolyte undergoes oxidation, whereas during discharge, the first redox active material present in the first aqueous electrolyte undergoes oxidation, and the second redox active material present in the second aqueous electrolyte undergoes reduction.

Figure 1A:
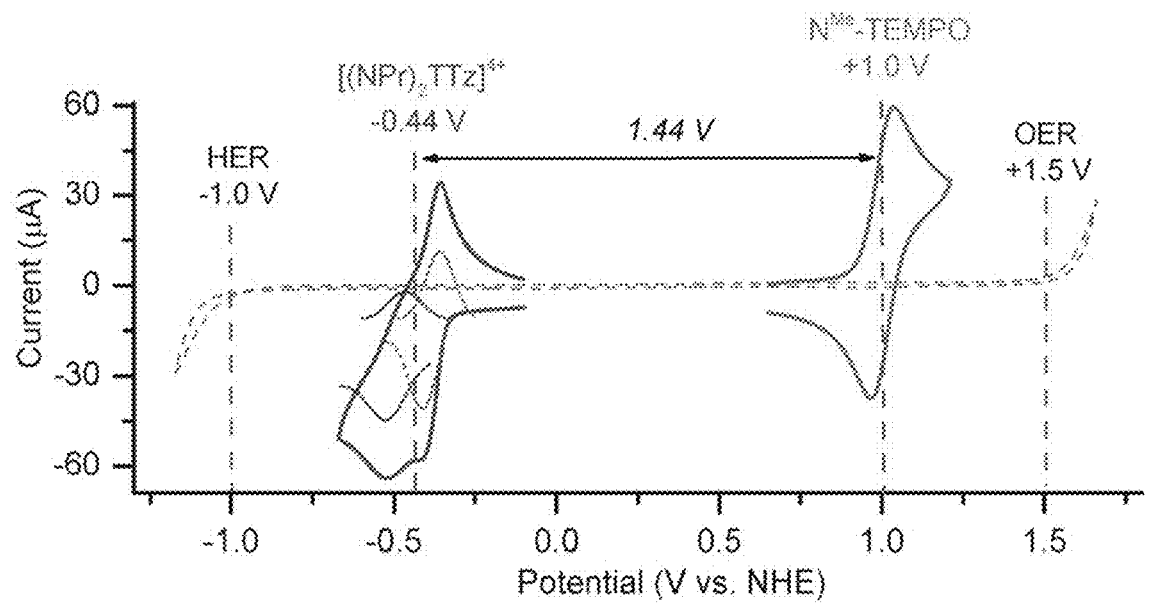
FIG. 1A shows cyclic voltammograms (CV) of 4.0 mm 4,4'-(thiazolo[5,4-d]thiazole-2,5-diyl)bis(1-(3-(trimethylammonio)propyl)pyridin-1-ium) tetrachloride ([(NPr)$_2$TTz]Cl$_4$) and 4.0 mm N$^{Me}$-TEMPO in 0.5 m NaCl solution. The dash curve is the cyclic voltammogram of only the 0.5 M NaCl electrolyte, with labels for the onset potentials for the hydrogen evolution reaction (HER, −1.00 V) and oxygen evolution reaction (OER, +1.50 V). The dash curves are the fitted redox waves for the 1$^{st}$ and 2$^{nd}$ electron reductions.
Figure 1B:
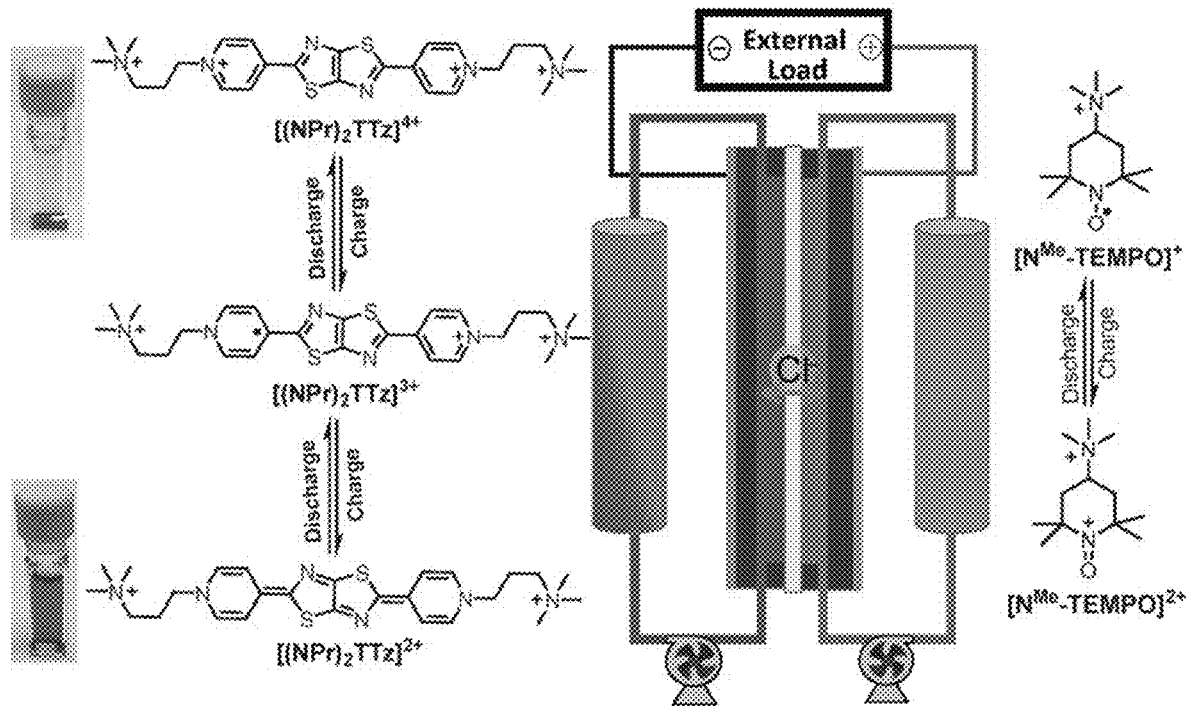
FIG. 1B shows a schematic representation of the [(NPr)$_2$TTz]$^{4+}$/N$^{Me}$-TEMPO AORFB (aqueous organic redox flow battery) and its anodic and cathodic half-cell reactions.

FIG. 1B shows an exemplary AORFB including a first electrolyte comprising $N^{Me}$-TEMPO as a first redox active material, and a second electrolyte comprising a viologen (4,4'-(thiazolo[5,4-d]thiazole-2,5-diyl)bis(1-(3-(trimethylammonio)propyl)pyridin-1-ium), [(NPr)$_2$TTz]) as a second redox active material, where an anion (e.g., Cl$^-$) exchanges between the first and second electrolytes to balance electroneutrality. During charge the redox material N$^{Me}$-TEMPO is oxidized (i.e., gives up an electron) and redox material [(NPr)$_2$TTz] is reduced (i.e., accepts an electron). To balance the charge from this electron transfer, an anion (e.g., Cl$^-$) is transported across the physical separator or anion-selective membrane. During discharge, when electricity is utilized from the battery, the current direction is reversed and redox materials N$^{Me}$-TEMPO and MV are reformed.

The exemplary AORFB in FIG. 1B also includes two circulation paths, each including a tank, pump, piping, and one or more chambers within an electrochemical stack. The electrochemical stack may include one or more electrochemical cells, wherein each electrolyte contacts either a positive or negative electrode and a separator divides the two electrolytes. In some embodiments, the separator is permeable to and/or conductive to ions.

A. Redox Active Materials

The disclosed AORFBs include first and second redox active materials. The redox active materials may have one or more redox potentials. In certain embodiments, the redox potentials of the first redox active material and second redox active material may be the same or different. When the potentials are different the type of redox active material with the higher potential is the "positive redox active material", and the corresponding electrolyte and electrode may be referred to as the "positive electrolyte" and "positive electrode". Likewise, the redox active material with the lower potential is the "negative redox active material," and the corresponding electrolyte and electrode may be referred to as the "negative electrolyte" and "negative electrode". During charge the positive redox active material present in the positive electrolyte undergoes oxidation, and the negative redox active material present in the negative electrolyte undergoes reduction, whereas during discharge, the positive redox active material present in the positive electrolyte undergoes reduction, and the negative redox active material present in the negative electrolyte undergoes oxidation.

First Redox Active Material

The first redox active material may comprise $^-$[Fe(CN)$_6$]$^{3+/2+}$, I$_3^-$/I$^-$, Br$_2$/Br$^-$, S$_4^-$/S$_2$, KBr, NaBr, NH$_4$Br, KI, NaI, NH$_4$I, FeCl$_2$, FeBr$_2$, Ce$^{4+/3+}$, Mn$^{3+/2+}$, PbO$_2$/PbSO$_4$, quinone, a derivative of quinone, anthraquinone, a derivative of anthraquinone, K$_4$[Fe(CN)$_6$], N$_4$[Fe(CN)$_6$], (NH$_4$)$_4$[Fe(CN)$_6$], Ni(OH)$_2$, V$^{5+/4+}$, (2,2,6,6-Tetramethylpiperidin-1-yl)oxyl (TEMPO), a derivative of TEMPO, or a combination thereof. The derivative of quinone can be (but not limited to) disodium 4,5-dihydroxy-1,3-benzenedisulfonate. The derivative of anthraquinone can be (but not limited to) anthraquinone-2,6-disulfonic acid and 2,6-dihydroxyanthraquinone.

The first redox active material may comprise a derivative of TEMPO selected from the group consisting of 4-trimethylammonium-(2,2,6,6-Tetramethylpiperidin-1-yl)oxy (4-N$^{Me}$-TEMPO), 4-dimethyl(propyl-3-N,N,N,-trimethyl-ammonium)-(2,2,6,6-Tetramethylpiperidin-1-yl)oxy ((4-N$^{NPr}$-TEMPO), 4-hyoxyl-ammonium-(2,2,6,6-Tetramethylpiperidin-1-yl)oxy (4-OHTEMPO), 4-sulfonate-(2,2,6,6-Tetramethylpiperidin-1-yl)oxy (4-SO$_3$-TEMPO), 4-amino-(2,2,6,6-Tetramethylpiperidin-1-yl)oxy (4-NH$_2$-TEMPO), N,N,N,2,2,6,6-heptamethylpiperidinyloxy-4-ammonium chloride (N$^{Me}$-TEMPO), and a combination thereof.

Second Redox Active Material

The second redox active material may comprise a viologen or salt thereof, wherein the viologen has the formula (I):

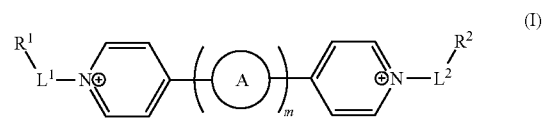

or a salt thereof, wherein:
m is 1, 2, or 3;
each A is independently selected from arylene or heteroarylene;
L$^1$ and L$^2$ are independently chosen from C$_1$-C$_{12}$ alkylene, C$_1$-C$_{12}$ alkenylene, C$_1$-C$_{12}$ alkynylene, —C$_1$-C$_4$ alkylene-(OCH$_2$CH$_2$)$_n$—, —C$_1$-C$_4$ alkylene-arylene-C$_1$-C$_4$ alkylene-, and —C$_1$-C$_4$ alkylene-arylene-(OCH$_2$CH$_2$)$_n$;
n, at each occurrence, is independently 1, 2, or 3;
R$^1$ and R$^2$ are independently selected from the group consisting of —CH$_3$, —NO$_2$, —OR$^a$, —C(O)R$^b$, —C(O)OR$^c$, —S(O)$_q$, —PO$_3$, —S(O)$_q$R$^d$, —S(O)$_q$OR$^e$, —OP(O)(OR)$_2$, —OCH$_2$, —P(O)(OR$^g$)$_2$, —CHO, —(CR$^h_2$)$_q$CN, —N(R$^i$)$_q$, and —P(R$^j$)$_r$;
each R$^a$, R$^b$, R$^c$, R$^d$, R$^e$, R$^f$, R$^g$, R$^h$, R$^i$ and R$^j$ are independently selected from the group consisting of hydrogen, C$_1$-C$_4$ alkyl, cycloalkyl, heterocyclyl, aryl, heteroaryl, C$_1$-C$_4$ alkyl-N(R$^k$)$_w$, C$_1$-C$_4$ alkyl-S(O)$_w$, an oxygen protecting group, and a nitrogen protecting group;
R$^k$, at each occurrence, is independently selected from the group consisting of hydrogen, alkyl, cycloalkyl, heterocyclyl, aryl, heteroaryl, an oxygen protecting group, and a nitrogen protecting group;
q, at each occurrence, is independently 2 or 3;
r, at each occurrence, is independently 2, 3, or 4; and
w, at each occurrence, is independently 2 or 3;
wherein each aryl, heteroaryl, arylene, heteroarylene, cycloalkyl, and heterocyclyl is independently unsubstituted or substituted.

In some embodiments, A is selected from the group consisting of:

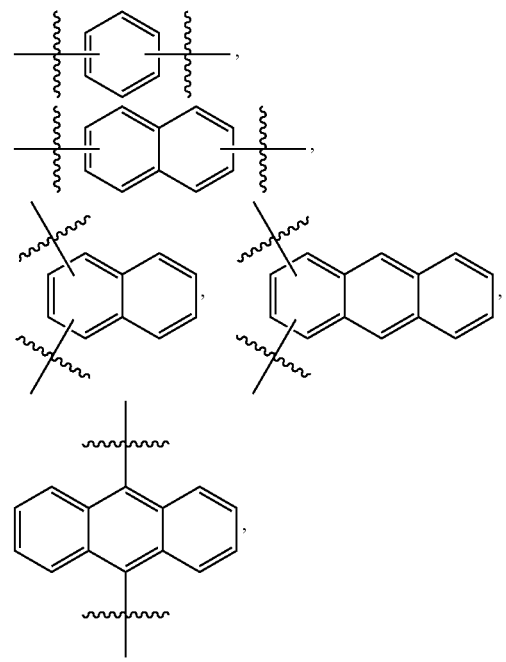

-continued

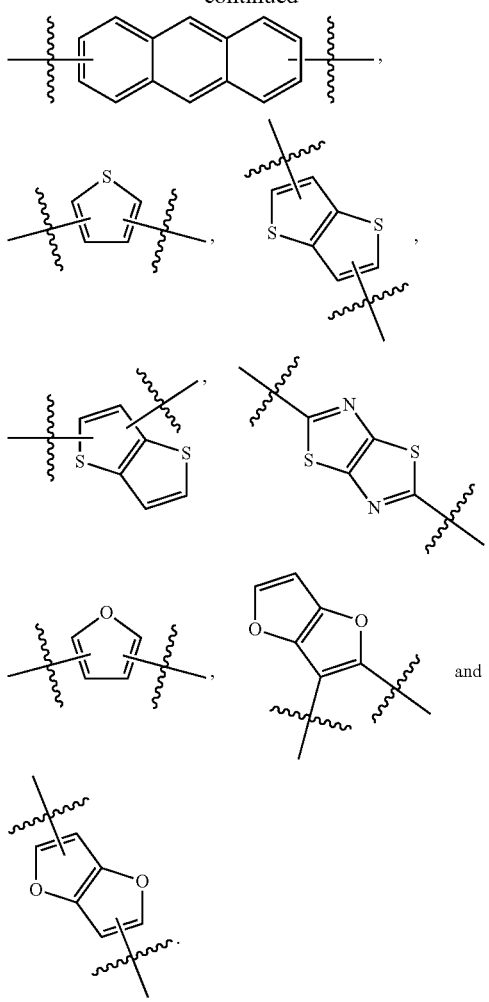

In some embodiments, A is

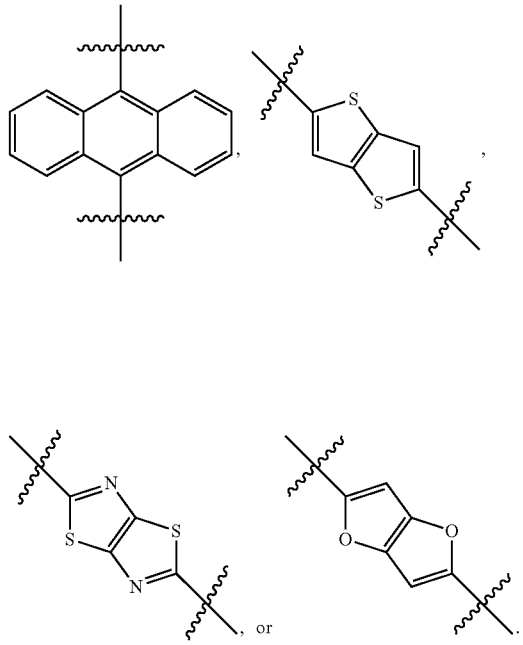

In some embodiments, A is

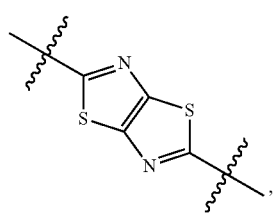 [SMILES: *c1nc2sc(*)nc2s1]

In some embodiments, m is 2 and A is a five-membered or six-membered arylene or heteroarylene. In certain embodiments, m is 2 and A is

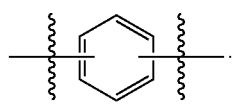

In some embodiments, $L^1$ and $L^2$ are independently $C_1$-$C_{12}$ alkylene. In some embodiments, $L^1$ and $L^2$ are independently $C_1$-$C_6$ alkylene. In some embodiments, $L^1$ and $L^2$ are $C_3$ alkylene.

In some embodiments, $L^1$ and $L^2$ are independently $C_1$-$C_{12}$ alkylene and A is

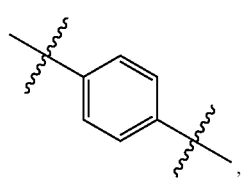

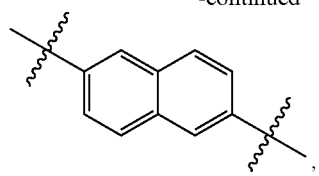 , 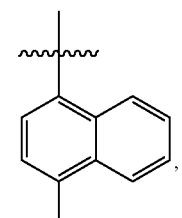 ,
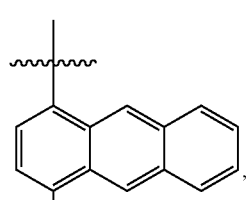 , 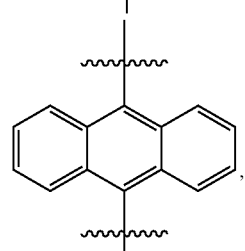 ,
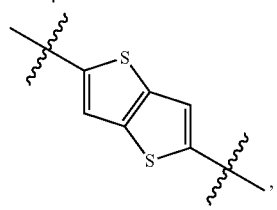 ,
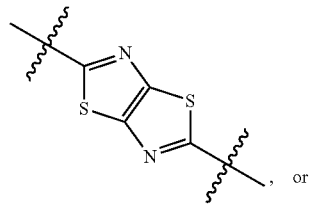 , or
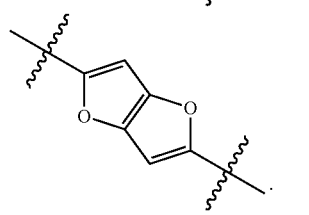 .
In some embodiments, $L^1$ and $L^2$ are independently $C_1$-$C_6$ alkylene and A is
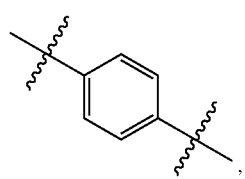 ,
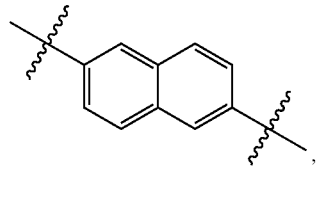 , 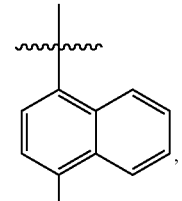 ,
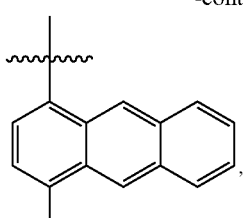 , 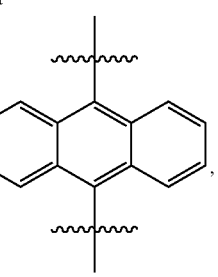 ,
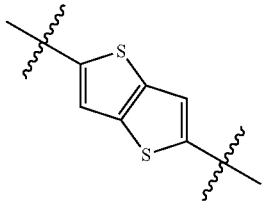 ,
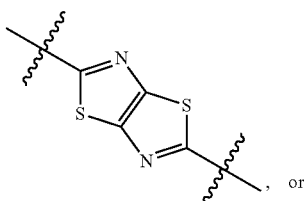 , or
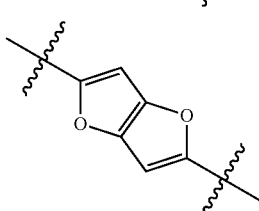 .
In some embodiments, $L^1$ and $L^2$ are $C_3$ alkylene and A is
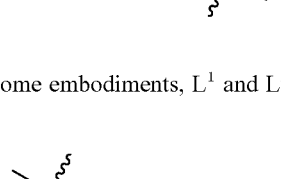 ,
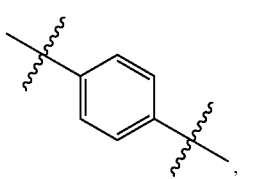 , 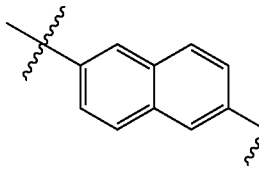 ,
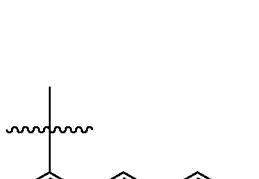 , 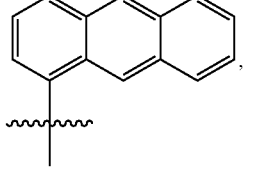 ,

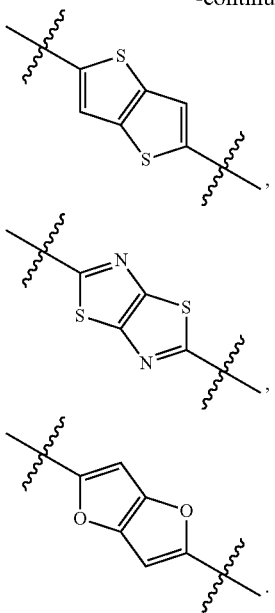

In some embodiments, $L^1$ and $L^2$ are $C_3$ alkylene and A is

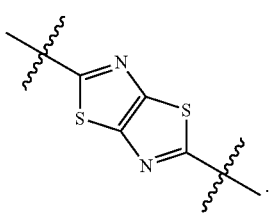 [SMILES: *c1nc2sc(*)nc2s1]

In some embodiments, $R^1$ and $R^2$ are independently selected from the group consisting of $—S(O)_q$, $—PO_3$, $—S(O)_qR^d$, and $—N(R^i)_q$ wherein $R^d$ and $R^i$ are independently selected from the group consisting of hydrogen, $C_1$-$C_4$ alkyl, cycloalkyl, heterocyclyl, aryl, heteroaryl, $C_1$-$C_4$ alkyl-$N(R^k)_w$, $C_1$-$C_4$ alkyl-$S(O)_w$, an oxygen protecting group, and a nitrogen protecting group and q is independently 2 or 3.

In some embodiments, each $R^a$, $R^b$, $R^c$, $R^d$, $R^e$, $R^f$, $R^g$, $R^h$, $R^i$ and $R^j$ are independently selected from hydrogen and $C_1$-$C_4$ alkyl.

In some embodiments, $R^1$ and $R^2$ are $N(R^i)_q$. In some embodiments, $R^1$ and $R^2$ are $—N(R_i)_q$ wherein $R^i$ is $C_1$-$C_4$ alkyl and q is 3. In certain embodiments, $R^1$ and $R^2$ are $—N(R^i)_q$ wherein $R^i$ is methyl and q is 3.

In some embodiments, $R^1$ and $R^2$ are independently selected from the group consisting of $—S(O)_q$, $—PO_3$, $—S(O)_qR^d$, and $—N(R^i)_q$, $L^1$ and $L^2$ are independently $C_1$-$C_{12}$ alkylene and A is

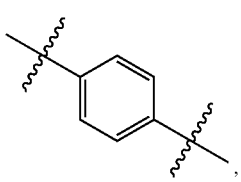

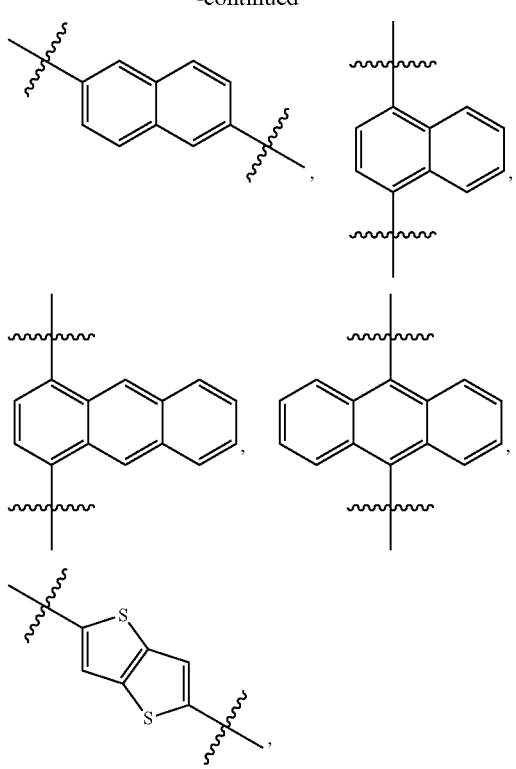

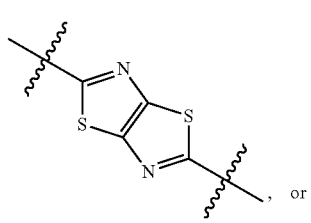

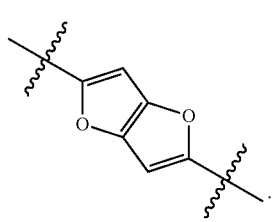

In some embodiments, $R^1$ and $R^2$ are independently selected from the group consisting of $—S(O)_q$, $—PO_3$, $—S(O)_qR^d$, and $—N(R^i)_q$, $L^1$ and $L^2$ are independently $C_1$-$C_6$ alkylene and A is

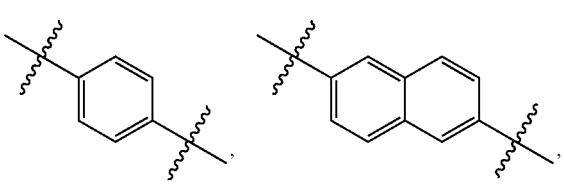

-continued

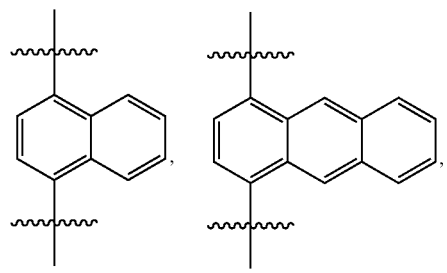

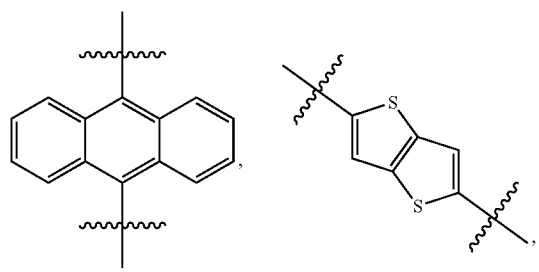

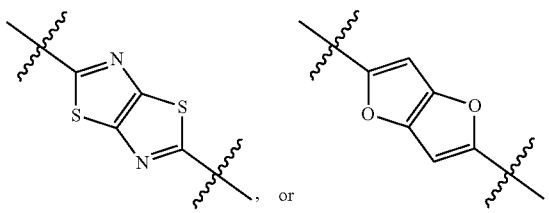

In some embodiments, $R^1$ and $R^2$ are independently selected from the group consisting of —S(O)$_q$, —PO$_3$, —S(O)$_q$R$^d$, and —N(R$^i$)$_q$, L$^1$ and L$^2$ are C$_3$ alkylene and A is

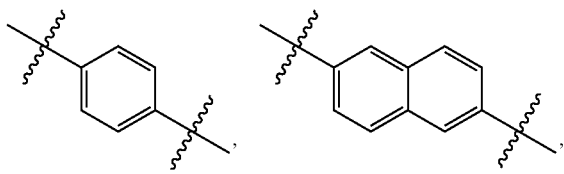

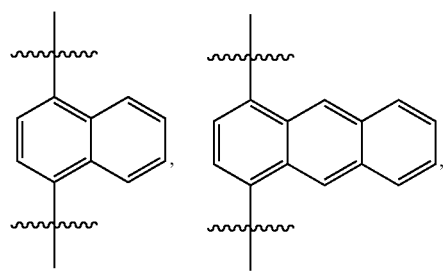

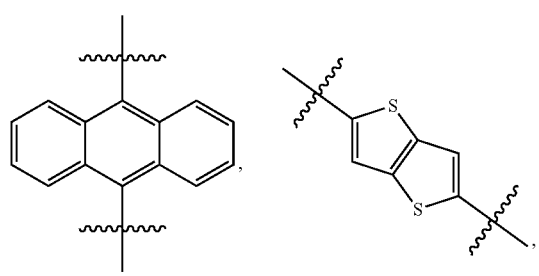

-continued

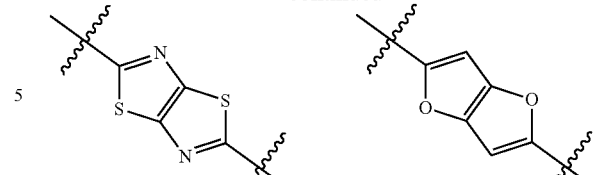

In some embodiments, $R^1$ and $R^2$ are —N(R$^i$)$_q$, L$^1$ and L$^2$ are C$_3$ alkylene and A is

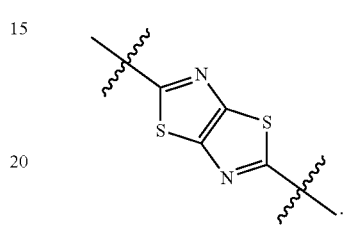

In certain embodiments, $R^1$ and $R^2$ are —N(CH$_3$)$_3$, L$^1$ and L$^2$ are C$_3$ alkylene and A is

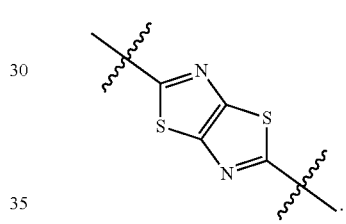

In some embodiments, the viologen of formula (I) is a salt of fluoride, chloride, bromide, iodide, hydroxide, sulfate, carbonate, chlorate, perchlorate, phosphate, dihydrogen phosphate, hydrogen phosphate, nitrate, nitride, nitrile, dicyanamide, thiocyanate, bis(trifluoromethane)sulfonamide, hexafluorophosphate, tetrafluorophosphite, or a combination thereof. In certain embodiments, the viologen of formula (I) is a salt of fluoride, chloride, bromide or iodide.

In some embodiments, the viologen of formula (I) may have an overall neutral charge (e.g., where the substituents balance the positive charge of the bipyridyl-core structure, such as when $R^1$ and $R_2$ are SO$_3^-$). In certain embodiments, a redox flow battery that includes a neutral viologen as the second redox material may also include K$_4$[Fe(CN)$_6$], KI or a combination thereof as the first redox active material. In certain embodiment, the first redox active material may include K$_4$[Fe(CN)$_6$], Na$_4$[Fe(CN)$_6$], (NH$_4$)[Fe(CN)$_6$] or a combination thereof. In certain embodiment, the first redox active material may include KI, NaI, (NH$_4$)I or a combination thereof.

B. Aqueous Electrolyte

The disclosed AORFBs may include an aqueous electrolyte(s). The disclosed AORFBs may include a first aqueous electrolyte and a second aqueous electrolyte. The redox active materials may be present in the aqueous electrolyte(s). For example, the first redox active material may be present in the first aqueous electrolyte and the second redox active material may be present in the second aqueous electrolyte. The first and second aqueous electrolytes may be the same or different. In certain embodiments, the first aqueous electrolyte is the positive electrolyte and the second aqueous electrolyte is the negative electrolyte. In other embodiments, the first aqueous electrolyte is the negative electrolyte and the second aqueous electrolyte is the positive electrolyte.

The first and second redox active materials may be present in the first and second aqueous electrolytes, respectively, at a concentration of ≥0.1 M, ≥0.2 M, ≥0.5 M, ≥1 M, ≥1.5 M, ≥2 M, ≥2.5 M, ≥3 M, ≥3.5 M, or ≥4 M. In certain embodiments, the first and second redox active materials may be present in the first and second aqueous electrolytes, respectively, at a concentration of from about 0.1 M to about 10 M, such as from about 0.1 M to about 8 M, from about 2 M to about 6 M, or from about 3 M to about 5 M.

The first and second aqueous electrolytes may include a salt. In certain embodiments, the first and second electrolytes may include a salt having the formula (II):

$$A\text{-}B \qquad (II),$$

wherein A is $Na^+$, $K^+$, $Li^+$, or $NR'''_4{}^+$, pyridinium, pyrrolidium, or imidazolium; $R'''$, is selected from the group consisting of hydrogen, an alkyl, a cycloalkyl, a heterocyclyl, an aryl, and a heteroaryl; and B is selected from the group consisting of a halide anion, $SO_4{}^{2-}$, $OH^-$, $CO_3{}^{2-}$, $ClO_4{}^-$, $H_2PO_4{}^-$, $HPO_4{}^{2-}$, $PO_4{}^{3-}$, $NO_3{}^-$, $N_3{}^-$, $CN^-$, $N(CN)_2{}^-$, or $SCN^-$. In certain embodiments, the first and second aqueous electrolytes include NaCl, KCl, or $NH_4Cl$.

In embodiments that include neutral viologen compounds as redox active materials, the first and second electrolyte each may individually include a salt where A is potassium. In certain embodiments, AORFBs that include neutral viologen compounds may also have first and second electrolytes that include KCl.

The salt may be present in the first and second aqueous electrolytes at a concentration of from about 0.5 M to about 5 M, such as from about 0.5 M to about 4 M, from about 1 M and about 3 M, or from about 0.5 M to about 2.5 M. In certain embodiments, the first and second aqueous electrolytes include from about 0.5 M to about 5 M NaCl, KCl, or $NH_4Cl$. In another embodiment, the first and second aqueous electrolytes include about 2 M NaCl, KCl, or $NH_4Cl$.

The first and second aqueous electrolytes may further include acids, bases, supporting electrolytes, additives, co-solvents or combinations thereof.

C. Separator

The disclosed AORFBs may include a separator. The separator may be a porous separator. The separator may not be permeable to the redox active materials (or salts thereof). In certain embodiments, the term separator is synonymous with membrane. Separators may be classified as permeable, semi-permeable, or non-permeable. The degree of permeability is dependent on the size of pores in the separator, the character (e.g., charge, hydrophobicity) of the pores, and the character of the electrolyte or electrolyte component which is to be transported across the separator. A porous separator is considered permeable to all electrolyte components, though the degree of permeability may differ for different component species of the electrolyte (e.g., based on size). A semi-permeable separator typically is selectively permeable to certain materials (e.g., small cations, small anions, $H_2O$) while being substantially non-permeable to other materials (e.g., large molecules, neutral species, and particular redox active materials). In certain embodiments, the separator is a non-porous separator permeable to ions.

The separator may be ion permeable. In certain embodiments, the separator is selectively permeable to permit the flux of cations with low resistance, and may be termed "cation permeable" or "cation conductive". In certain embodiments, the separator is selectively permeable to permit the flux of anions with low resistance, and may be termed "anion permeable" or "anion conductive". Accordingly, the separator may be cation permeable or anion permeable. An ion selective separator may comprise functional groups of opposite charge to the permitted ion, such that the charge of the functional group repels ions of like charge. In certain embodiments, the separator is a cation exchange membrane. In certain embodiments, the separator is an anion exchange membrane. In other embodiments, the separator is a sulfonate containing fluoropolymer, such as NAFION®. In still other embodiments, the separator is a sulfonated poly(ether ether ketone), polysulfone, polyethylene, polypropylene, ethylene-propylene copolymer, polyimide, or polyvinyldifluoride. In some embodiments, the separator is functionalized with ammonium, $SO_3H$, OH, COOH or a combination thereof.

The separator may include an ion conductive ceramic, zeolite, or glass. Ion conductive ceramics, zeolites, and glasses are solid materials in which certain ions have high mobility. In certain embodiments, an ion conductive ceramic, zeolite, or glass is permeable to a flux of a certain ion (e.g., $Li^+$, $Na^+$, $K^+$) but may be substantially non-permeable to a flux of another ion (e.g., $H^+$). In certain embodiments, an ion conductive solid ceramic, zeolite, or glass is utilized to maintain a pH imbalance between the first and second electrolytes. In certain embodiments, the separator includes a cation conducting ceramic, zeolite, or glass. In certain embodiments, the separator includes an anion conducting ceramic, zeolite, or glass.

The separator may include one or more separator materials. In certain embodiments, the separator includes multiple components. For example, the separator may include two or more layered membranes or a coated membrane. In certain embodiments, the separator includes a porous membrane coated with a cation or anion conducting ceramic, zeolite, or glass. In other embodiments, the separator comprises an ionic exchange membrane coated with a cation or anion conducting ceramic, zeolite, or a glass.

The separator may have a thickness of ≤200 microns, ≤100 microns, ≤50 microns, or ≤25 microns. In certain embodiments, the separator has a thickness of ≥10 microns, ≥15 microns, ≥25 microns or ≥50 microns. In certain embodiments, the separator has a thickness of from about 10 microns to about 200 microns, such as from about 10 microns to about 100 microns or from about 25 microns to about 100 microns.

D. Electrodes

The disclosed AORFBs may include one or more electrodes. In certain embodiments, the disclosed AORFBs include a first electrode and a second electrode. The first and second electrode may be the same material, or they may be different materials. In certain embodiments, the electrodes may include a carbon felt, carbon mesh, carbon foam, carbon cloth, carbon paper, or carbon plate. The electrode or electrodes may be coated with a catalyst to improve the efficiency of charge transfer at the electrode, for example, to reduce the charging and/or discharging overpotential. The electrode or electrodes may be coated with a poison, such as lead, to reduce the efficiency of current transfer, for example to reduce the current density of the hydrogen evolution reaction.

Each electrode may in contact with an electrolyte. In certain embodiments, the first electrode may be in contact with the first aqueous electrolyte. In certain embodiments, the second electrode may be in contact with the second aqueous electrolyte.

E. Properties of the Aqueous Organic Redox Flow Batteries

The disclosed AOFRBs have advantageous electrochemical properties. Some of these exemplary properties are listed below.

The AOFRB may have an energy density of ≥5 Wh/L, ≥10 Wh/L, ≥20 Wh/L, ≥30 Wh/L, ≥40 Wh/L ≥50 Wh/L, ≥75 Wh/L, ≥100 Wh/L, or ≥150 Wh/L. In certain embodiments, the AOFRB may have an energy density of from about 10 Wh/L to about 200 Wh/L, such as from about 30 Wh/L to about 150 Wh/L or from about 50 Wh/L to about 100 Wh/L.

The AOFRB may have from about 90% total capacity retention to about 99.9% total capacity retention after at least 300 cycles at 40 mA/cm$^2$, such as from about 92% total capacity retention to about 99.9% total capacity retention, from about 93% total capacity retention to about 99.9% total capacity retention, or from about 95% total capacity retention to about 99.9% total capacity retention after at least 300 cycles at 40 mA/cm$^2$.

The AOFRB may be operated at a current density of ≥25 mA/cm$^2$, ≥50 mA/cm$^2$, ≥75 mA/cm$^2$, ≥100 mA/cm$^2$, ≥125 mA/cm$^2$, or ≥150 mA/cm$^2$. In addition, the AOFRB may be operated at a power density of ≥50 mW/cm$^2$, ≥100 mW/cm$^2$, ≥125 mW/cm$^2$, ≥150 mW/cm$^2$, ≥175 mW/cm$^2$, ≥200 mW/cm$^2$, ≥225 mW/cm$^2$, or ≥250 mW/cm$^2$.

The AOFRB may have an energy efficiency of about 50% to about 99.9%, such as from about 70% to about 99.9%, from about 70% to about 95%, or from about 70% to about 80%.

In certain embodiments, the AOFRB has a Coulombic efficiency of about 100%.

4. Methods of Use

The disclosed AOFRBs may be used to store and release energy. A method of storing energy comprises applying a potential difference across the first and second electrode of the redox flow battery disclosed herein, wherein the first redox active material is oxidized. A method of releasing energy comprises applying a potential difference across the first and second electrode of the redox flow battery disclosed herein, wherein the first redox active material is reduced.

5. Examples

For the following examples, all chemicals were purchased from Sigma-Aldrich or TCI Chemicals, stored in an argon glovebox, and used directly. Deionized water was purged overnight using $N_2$ before use. All battery tests were conducted under a $N_2$ atmosphere. $^1$H-NMR and $^{13}$C-NMR spectrum were collected using a Bruker 500 MHz NMR spectrometer. Elemental analysis was performed by Atlantic Microlab. All electrochemical experiments were conducted with a Gamry 1000E potentiostat. Battery tests were performed using a Land battery testing system.

Example 1: Compound Synthesis

Methyl viologen ($MV^{2+}$) exhibits two single-electron reductions at −0.45 V and −0.76 V (vs. NHE). However, only the reversible $MV^{2+/+}$ redox couple has been utilized in the battery charge/discharge process, due to the insolubility of the charge-neutral $MV^0$ state in aqueous solution. Meanwhile, the reduced states of MV ($MV^+$ and $MV^0$) are highly air sensitive, which may affect the stability and energy efficiency of flow batteries. "Extended viologens" are conjugation-extended viologens in which two pyridinium moieties are linked by a central π-conjugated framework. With the extension of the skeletal structure of 4,4'-bipyridinium of viologen, the reductive potential gap between the $1^{st}$ and $2^{nd}$ electron reduction can be reduced due to a larger π-conjugated system, which would enable viologen-based batteries to deliver more uniform battery voltages. More importantly, the stability of the reduced species can be enhanced by the strategy of π-conjugated extension. Thiazolo[5,4-d]thiazole (TTz) is a rigid aromatic bicyclic framework that has been widely applied in the organic semiconductor, and it can be easily synthesized by double condensation of aromatic aldehyde with dithiooxamide. TTz is a good extending framework for viologen compounds due to its planar structure that is beneficial for the electronic communication of a conjugated system.

N,N'-dimethylated dipyridinium thiazolo[5,4-d]thiazole dichloride (($Me_2TTz$)$Cl_2$) was synthesized as shown in Scheme 1. Unfortunately, due to the high rigidity and hydrophobicity of the $Py_2TTz$ skeleton, ($Me_2TTz$)$Cl_2$ has poor water solubility (<10 mm in water). Incorporation of highly hydrophilic groups such as ammonium, sulfonate, and phosphate, may be an efficient strategy to improve the water solubility of redox active organic compounds for AORFB applications. As shown in Scheme 1, a highly hydrophilic ammonium functional group was applied to functionalize the N atoms of the pyridine to overcome the solubility issue of the $TTz^{2+}$.

Scheme 1

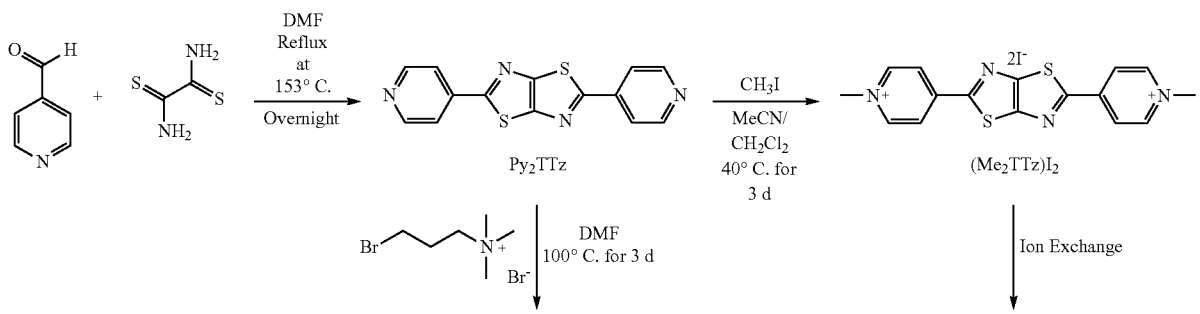

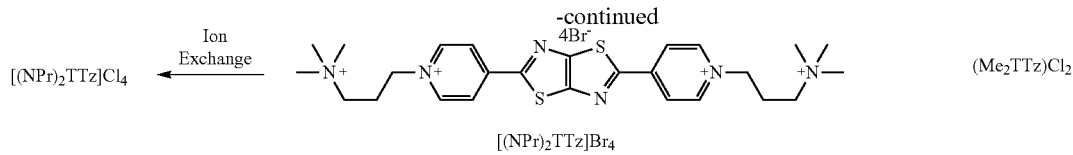

As shown in Scheme 1, the Py$_2$TTz was functionalized with hydrophilic 3-(trimethylaminium)propyl (NPr) pendant arms to get the water-soluble 4,4'-(thiazolo[5,4-d]thiazole-2,5-diyl)bis(1-(3-(trimethylammonio)propyl)pyridin-1-ium) tetrachloride ([(NPr)$_2$TTz]Cl$_4$). Py$_2$TTz was refluxed with (3-bromopropyl)trimethylammonium bromide in DMF to precipitate the 4,4'-(thiazolo[5,4-d]thiazole-2,5-diyl)bis(1-(3-(trimethylammonio)propyl)pyridin-1-ium) tetrabromide ([(NPr)$_2$TTz]Br$_4$). Then, anion exchange was conducted to quantitatively convert [(NPr)$_2$TTz]Br$_4$ to the chloride version, [(NPr)$_2$TTz]Cl$_4$, to avoid the influence of redox active bromide in battery tests. The synthesis of [(NPr)$_2$TTz]Cl$_4$ was demonstrated up to a 20 g scale through a three-step synthetic route with 63% overall isolated yield. The product was characterized by $^1$H-, $^{13}$C-NMR, and elemental analysis.

Synthesis of 2,5-di(pyridine-4-yl)thiazolo[5,4-d]thiazole, Py$_2$TTz rA solution of rubeanic acid (10.0 g, 83.4 mmol) and 4-pyridinecarboxaldehyde (20 mL, 216 mmol) was refluxed in 400 mL DMF at 153° C. overnight under air. The reaction mixture was cooled to room temperature, and then the obtained precipitate was filtered, washed with water, and then dried under vacuum to get the product as light yellow solids. 19.2 g, 77% yield.

$^1$H-NMR (CDCl3, 500 MHz): δ (ppm), 7.92 (d, J=4.5 Hz, 2H), 8.81 (d, J=4.5 Hz, 2H). Elemental analysis for C$_{14}$H$_8$N$_4$S$_2$, calculated: C, 56.74; H, 2.72; N, 18.91. Found: C, 56.60, H, 2.87, N, 18.83.

Synthesis of N,N'-dimethyl 2,5-bis(4-pyridinium) thiazolo[5,4-d]thiazole Diiodine, (Me$_2$TTz)I$_2$ In a 100 mL N$_2$ purged flask, Py$_2$TTz (0.5 g, 1.7 mmol) and CH$_3$I (0.42 mL, 6.8 mmol) was stirred in a 40 mL MeCN/CH$_2$Cl$_2$ (1:1 v/v) solution at 40° C. for 3 days. The reaction mixture was cooled to room temperature, and then the resulting precipitate was filtered and washed with CH$_2$Cl$_2$ to get the product as red crystals.

$^1$H-NMR (D$_2$O, 500 MHz): δ (ppm), 4.38 (s, 6H), 8.57 (d, J=5.5 Hz, 4H), 8.88 (d, J=5.5 Hz, 4H). Elemental analysis for C$_{16}$H$_{16}$I$_2$N$_4$OS$_2$ ((Me$_2$TTz)I$_2$+H$_2$O), calculated: C, 32.12; H, 2.70; N, 9.37. Found: C, 32.13, H, 2.80, N, 9.11.

Synthesis of N,N'-dimethyl 2,5-bis(4-pyridinium) thiazolo[5,4-d]thiazole Dichloride, (Me$_2$TTz)Cl$_2$ The iodine ions of (Me$_2$TTz)I$_2$ were exchanged for chloride by column anion exchange with Amberlite® IRA-900 chloride form anion exchange resin to give (Me$_2$TTz)Cl$_2$ with 100% yield. Cyclic voltammetry was applied to validate the complete replacement of iodide. (Me$_2$TTz)Cl$_2$ displayed identical $^1$H-NMR resonances as (Me$_2$TTz)I$_2$. Elemental analysis for C$_{16}$H$_{16}$Cl$_2$N$_4$OS$_2$ ((Me$_2$TTz)Cl$_2$+H$_2$O), calculated: C, 46.27; H, 3.88; N, 13.49. Found: C, 46.29, H, 3.94, N, 13.28.

Synthesis of 4,4'-(thiazolo[5,4-d]thiazole-2,5-diyl) bis(1-(3-(trimethylammonio)propyl)pyridin-1-ium) Tetrabromide, [(NPr)$_2$TTz]Br$_4$ In a 500 mL N$_2$ purged Schlenk flask, Py$_2$TTz (15.0 g, 50.7 mmol) was combined with (3-bromopropyl)trimethylammonium bromide (33.0 g, 126.6 mmol) in 300 mL DMF, and stirred at 100° C. for 3 days. The resulting light yellow precipitate was filtered and washed with 50 mL cold DMF and 3×80 mL acetonitrile, then dried under vacuum. 33.6 g, 81% yield. $^1$H-NMR (D$_2$O, 500 MHz): δ (ppm), 2.62 (m, 4H), 3.14 (s, 18H), 3.53 (t, J=8.0 Hz, 4H), 4.74 (t, J=6.5 Hz, 4H), 8.66 (d, J=5.5 Hz, 4H), 9.02 (d, J=5.5 Hz, 4H). $^{13}$C-NMR (D$_2$O, 125 MHz): δ (ppm), 24.6, 53.2, 57.9, 62.5, 124.9, 145.4, 147.7, 155.7, 165.3.

Elemental analysis for C$_{26}$H$_{44}$Br$_4$N$_6$O$_3$S$_2$ ([(NPrPy)$_2$TTz]Br$_4$+3H$_2$O), calculated: C, 35.80; H, 5.08; N, 9.63. Found: C, 35.67; H, 5.16; N, 9.58.

Synthesis of 4,4'-(thiazolo[5,4-d]thiazole-2,5-diyl) bis(1-(3-(trimethylammonio)propyl)pyridin-1-ium) Tetrachloride, [(NPr)$_2$TTz]Cl$_4$ The bromide ions of [(NPrPy)$_2$TTz]Br$_4$ were exchanged for chloride by column anion exchange with Amberlite® IRA-900 chloride form anion exchange resin to give [(NPrPy)$_2$TTz]Cl$_4$. Cyclic voltammetry was applied to validate the complete replacement of bromide. 26.2 g, 100% yield. [(NPrPy)$_2$TTz]Cl$_4$ displayed identical $^1$H-NMR and $^{13}$C-NMR resonances as [(NPrPy)$_2$TTz]Br$_4$.

Elemental analysis for C$_{26}$H$_{47}$Cl$_4$N$_6$O$_{4.5}$S$_2$ ([(NPrPy)$_2$TTz]Cl$_4$+4.5H$_2$O), calculated: C, 43.28; H, 6.57; N, 11.65. Found: C, 43.12; H, 6.18; N, 11.60.

Synthesis of 3,3'-(thiazolo[5,4-d]thiazole-2,5-diylidenebis(pyridin-1(4H)-yl-4(4H)-ylidene))bis(N,N,N-trimethylpropan-1-aminium) Dichloride, [(NPr)$_2$TTz]Cl$_2$

[(NPr)$_2$TTz]Cl$_2$ was prepared by chemical reduction of [(NPr)$_2$TTz]Cl$_4$. Under N$_2$, 10 mg of [(NPr)$_2$TTz]Cl$_4$ was dissolved in 1.0 mL MeOH, and then 50 mg Zn powder was added, leading to solution color change to purple immediately. The mixture was stirred at room temperature for 12 h. After removing Zn powder by filtration, the solvent was removed under vacuum.

$^1$H-NMR (D$_2$O, 500 MHz): δ (ppm), 2.52 (brs, 4H), 3.10 (s, 18H), 3.45 (brs, 4H), 4.55~4.68 (m, 4H), 7.77~8.10 (m, 4H), 8.53~8.86 (m, 4H). $^{13}$C-NMR (D$_2$O, 125 MHz): δ (ppm), 24.5, 53.1, 57.2, 62.5, 126.4, 129.0, 143.2, 143.8, 144.0.

Synthesis of N, N, N, 2, 2, 6, 6-Heptamethylpiperidinyloxy-4-ammonium Chloride (N$^{Me}$-TEMPO)

2,2,6,6-Tetramethyloxy-4-aminopiperidine (1.71 g, 10 mmol) and methyl iodide (8.52 g, 60 mmol) were dissolved in 20 mL acetone. The solution was stirred at room temperature overnight. The generated orange precipitate was filtered and washed by 5.0 mL acetone three times. After dried, the obtained orange powder was dissolved in 10.0 mL deionized water and flushed through an anion exchange column with Amberlite® IRA-900 chloride form anion exchange resin. Cyclic voltammetry was applied to validate the replacement of iodide. After removing water under vacuum, the product was obtained as an orange powder (0.91 g, 36.4%). 1H NMR (500 MHz, D$_2$O with one drop of phenylhydrazine): δ (ppm), 3.53 (t, J=12.6 Hz, 1H), 2.89 (s, 9H), 2.01 (d, J=11.9 Hz, 2H), 1.59 (t, J=12.2 Hz, 2H), 1.15 (s, 6H), 1.09 (s, 6H). Elemental analysis of C$_{12}$H$_{20}$N$_2$OCl (N$^{Me}$-TEMPO), calculated: C, 55.72; H, 10.42; N, 11.22. Found C, 55.63; H, 10.51; N, 11.14.

Example 2: Manufacturing Cost Calculation

In comparison to inorganic Vanadium ARFBs, the estimated material cost of [(NPr)$_2$TTz]Cl$_4$ (ca. \$2.3 kg$^{-1}$) is only one tenth of the V$_2$O$_5$ (ca. 24 kg$^{-1}$).

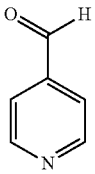

| | | | | |
|---|---|---|---|---|
| Ratio | 2.5 eq | 1.0 eq | 2.5 eq | 0.63 eq (63% yield) |
| MW: | 107 g/mol | 120 g/mol | 261 g/mol | 640 g/mol |
| Chemical Price: | 1.0 USD/kg 0.107 USD/mol | 1.0 USD/kg 0.120 USD/mol | 1.0 USD/kg 0.215 USD/mol | Cost: 2.29 USD/kg 1.47 USD/mol |

Example 3: Characterization of [(NPr)$_2$TTz]Cl$_4$

The highly charged ionic [(NPr)$_2$TTz]Cl$_4$ exhibited a high solubility in aqueous solution, 1.3 m in H$_2$O (69.7 Ah L$^{-1}$) or 1.1 m in 2.0 m NaCl (60.0 Ah L$^{-1}$).

Cyclic voltammetry was further used to characterize [(NPr)$_2$TTz]Cl$_4$.r All cyclic voltammetry experiments were conducted in an N$_2$ purged 0.5 M NaCl aqueous solution with a Gamry 1000E potentiostat. A 3 mm PEEK encased glassy carbon disk was used as the working electrode. The working electrode was polished with 0.05 micron Al$_2$O$_3$ powder and rinsed with deionized H$_2$O. A glassy carbon rod was used as the counter electrode. A silver wire coated with AgCl and suspended in 3.0 M KCl electrolyte was used as the reference electrode. The two redox peaks of [(NPr)$_2$TTz] Cl$_4$ were distinguished by peak fitting of its CV curve in the Origin program after removing background current.

Figure 3:
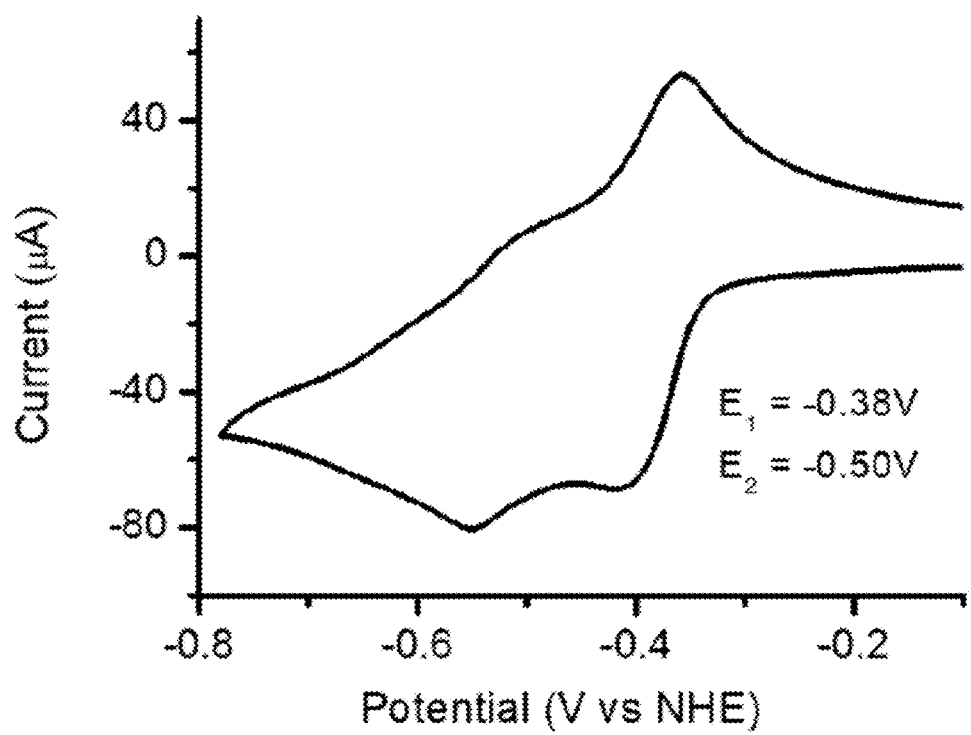
FIG. 3 shows the cyclic voltammetry (CV) of 4.0 mM [(NPr)$_2$TTz]Cl$_4$ in a 0.5 M NaCl solution (Scan rate: 100 mV/s).
Figure 4A:
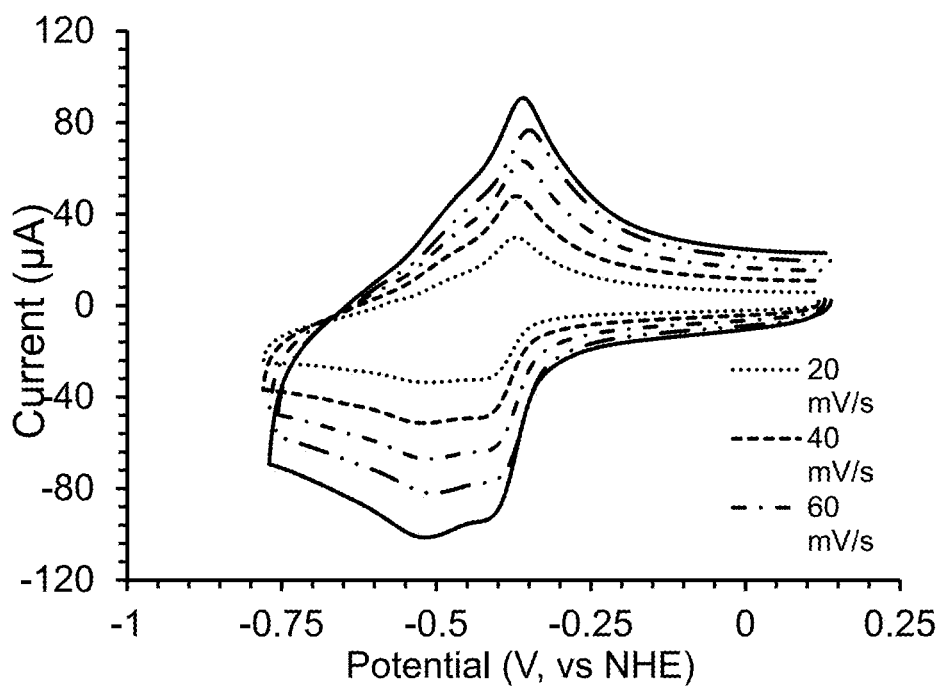
FIG. 4A and FIG. 4B show cyclic voltammetry (CV) of 4.0 mM [(NPr)$_2$TTz]Cl$_4$ in a 0.5 M NaCl solution with a scan rate between 20 and 100 mV/s (FIG. 4A) and a plot of i vs. v$^{1/2}$.
Figure 4B:
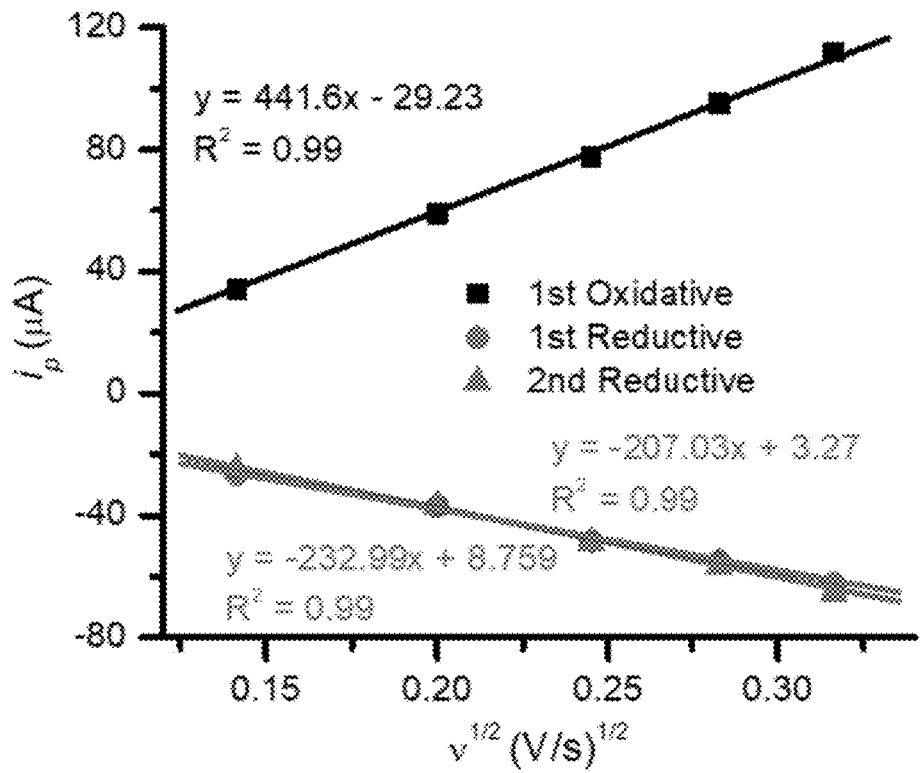

The cyclic voltammogram (CV) of [(NPr)$_2$TTz]Cl$_4$ showed two reversible redox waves at −0.38 V vs. NHE for E$_{1/2}$([(NPr)$_2$TTz]$^{4+/3+}$) and −0.50 V vs. NHE for E$_{1/2}$ ([(NPr)$_2$TTz]$^{3+/2+}$) (FIG. 1A and FIG. 3), respectively. Under different scan rates, the peak currents of these two redox processes of [(NPr)$_2$TTz]Cl$_4$ showed a linear relationship with the square root of scan rate (v$^{1/2}$, FIG. 4A and FIG. 4B), which indicated both redox couples of [(NPr)$_2$TTz]$^{4+/3+}$ and [(NPr)$_2$TTz]$^{3+/2+}$ were reversible and were diffusion controlled.

Example 4: Electrochemical Rotating Disk Electrode Studies

To further qualify the [(NPr)$_2$TTz]Cl$_4$ as an anolyte candidate for AORFBs, the diffusion coefficient (D) was investigated using linear sweep voltammetry (LSV) with a glassy carbon rotating disk electrode.

Linear sweep voltammetry (LSV) experiments were conducted using a Gamry 1000E potentiostat with a three-electrode system. A 5 mm diameter rotating glassy carbon disk encased in Teflon served as the working electrode. A glassy carbon rod was used as the counter electrode. An Ag/AgCl wire served as the reference electrode. The working electrode was cleaned using the same method as in the CV experiments. During the experiments, the working electrode rotated from 300 rpm to 2400 rpm at increments of 300 rpm. Three scans at each rotation rate were collected to ensure accuracy. LSV scans were conducted at a rate of 5 mV/s from 0.2 V to 0.8 V versus NHE. Due to the overlap of the 1$^{st}$ and 2$^{nd}$ electron reductions, the limiting currents (mass transport-limited current intensity) at each rotation rate were recorded at 0.70 V versus NHE to calculate the average diffusion coefficient of [(NPr)$_2$TTz]$^{4+}$ and [(NPr)$_2$TTz]$^{3+}$.

The Levich plots of limiting current versus square root rotation rate showed linear relationships. The slopes of these fitted lines are defined by the Levich equation, Levich Plot Slope=0.620nFAC$_0$D$^{2/3}$D$^{1/6}$     (Equation 1)

where n=2 for a two electron process, Faraday's constant F=96485 C/mol, electrode area A=0.1963 cm$^2$, [(NPr)$_2$TTz] Cl$_4$ concentration C$_0$=1×10$^{-6}$ mol/cm$^3$, D represents the diffusion coefficient, and the kinematic viscosity of 0.5 M NaCl aqueous solution ν=0.009 cm$^2$/s.

Figure 5A:
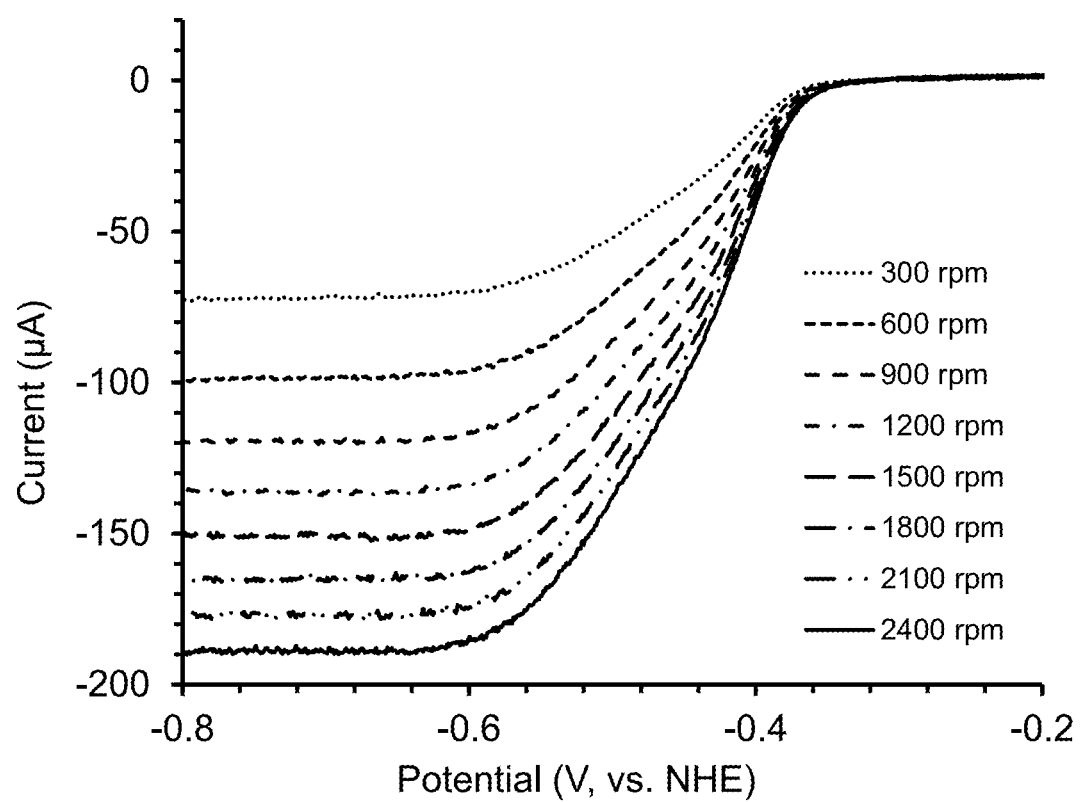
FIG. 5A and FIG. 5B show RDE curves of 1.0 mM [(NPr)$_2$TTz]Cl$_4$ in a 0.5M NaCl solution (FIG. 5A) and a plot of i vs. w$^{1/2}$ (FIG. 5B).
Figure 5B:
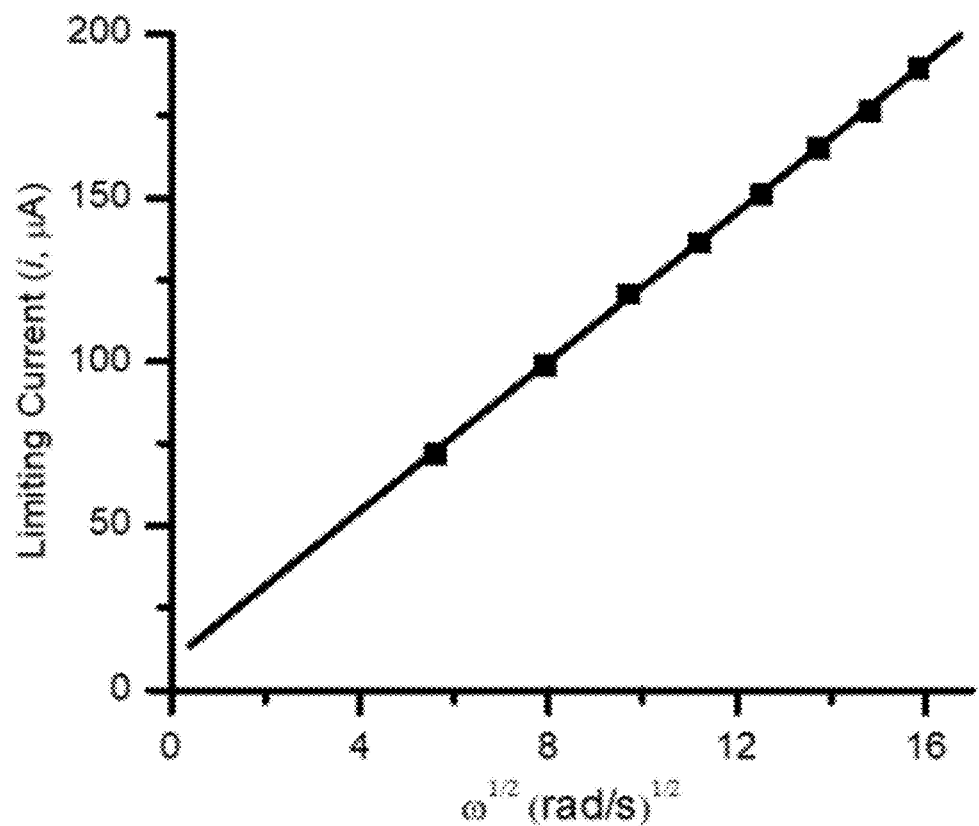

LSV plots, and derived Levich plot for [(NPr)$_2$TTz]Cl$_4$ are shown in FIG. 5A and FIG. 5B. Due to the near redox potentials of the two single-electron reductions (−0.38 V for the 1$^{st}$ electron and −0.50 V for the 2$^{nd}$ electron), there was only one plateau observed in the LSV curves (FIG. 5A). The linear Levich plot (FIG. 5B) was constructed for the combined single-electron reductions of [(NPr)$_2$TTz]$^{4+}$ and [(NPr)$_2$TTz]$^{3+}$ using limiting currents (i) and the square root of rotation speeds (ω$^{1/2}$). The corresponding slope from the linear relationship was transformed using the Levich equation (Equation 1) to calculate the average diffusion coefficient for [(NPr)$_2$TTz]$^{4+}$ and [(NPr)$_2$TTz]$^{3+}$ as 3.15×10$^{-6}$ cm$^2$ s$^{-1}$.

Example 5: Electron Transfer Rate Constants

Figure 6A:
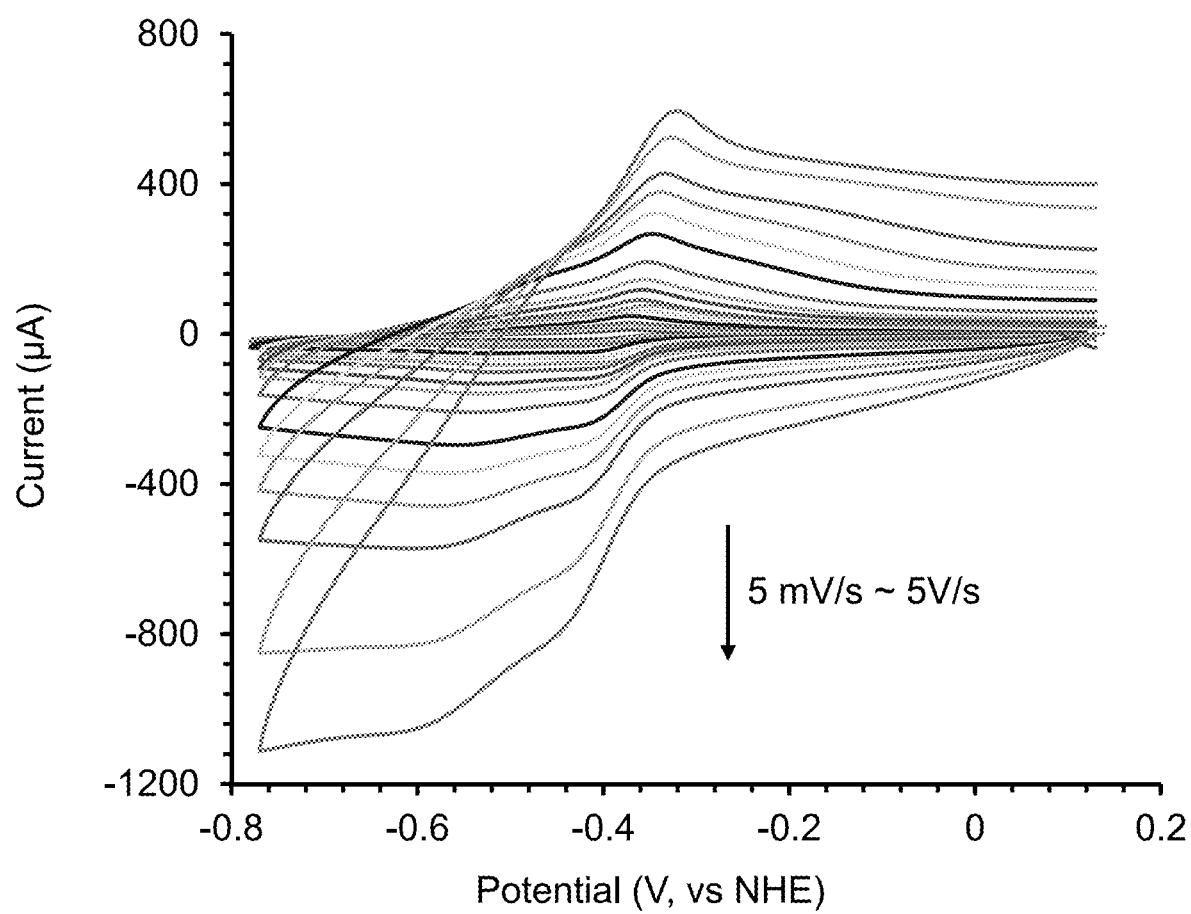
FIG. 6A and FIG. 6B show CV curves of 4.0 mM [(NPr)$_2$TTz]Cl$_4$ in a 0.5M NaCl solution with a scan rate of 5 mV/s to ~5 V/s (FIG. 6A) and 500 mV/s (FIG. 6B).
Figure 6B:
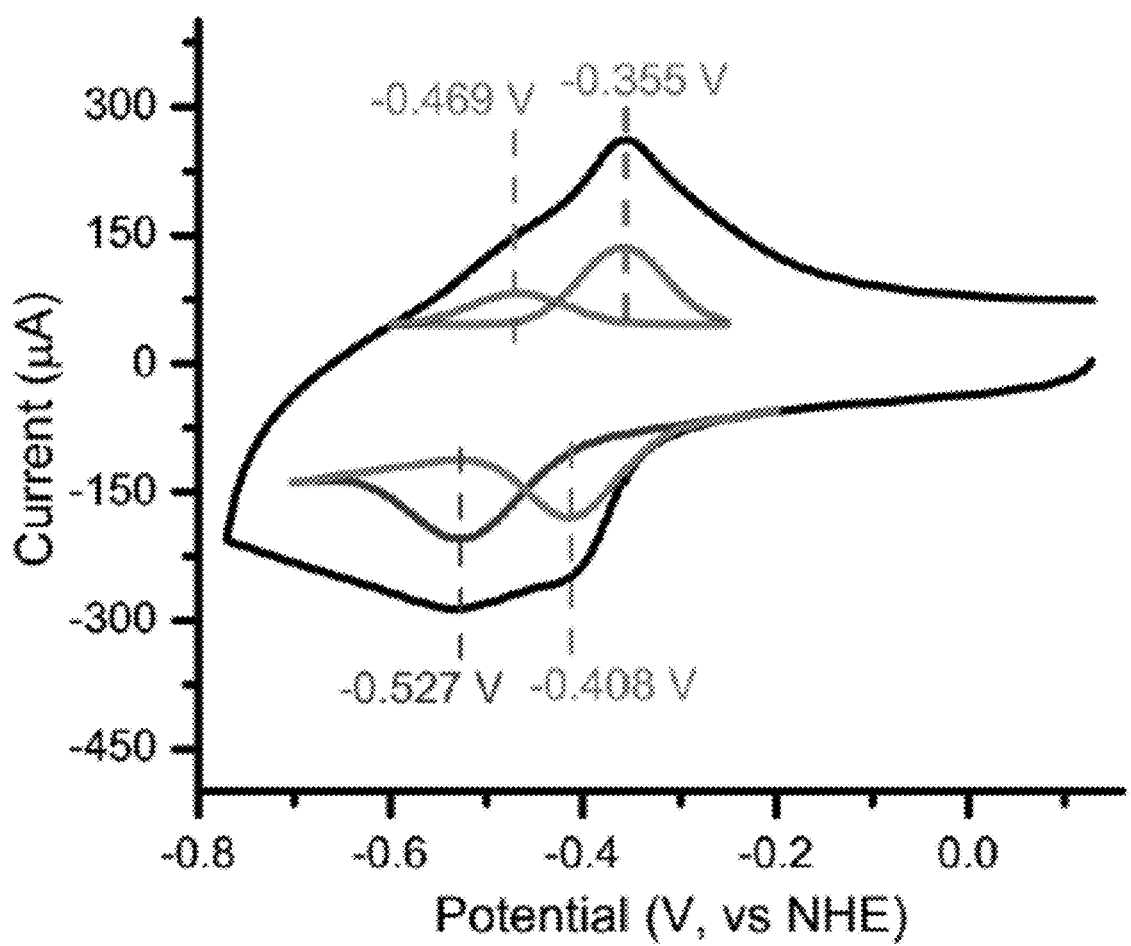

The electron transfer rate constants (k$^0$) for the electron transfers of [(NPr)$_2$TTz]$^{4+}$ and [(NPr)$_2$TTz]$^{3+}$ were estimated. Following the well-known Nicholson's method (R. S. Nicholson, *Anal. Chem.* 1965, 37, 1351-1355.), a solution containing 4.0 mM [(NPr)$_2$TTz]Cl$_4$ with 0.5 M NaCl was used to record CV curves (FIG. 6A and FIG. 6B). The peak-to-peak separation (reduction and oxidation peak potential gap), $\Delta E_p$, was obtained and used to calculate the kinetic parameter, $\Psi$, using Equation 2. And then, $k^0$ was calculated from equation 3 based on the relationship between $\Psi$ and $v^{-1/2}$.

$$\Psi=(-0.6288+0.0021\Delta E_p)/(1-0.017\Delta E_p) \quad \text{(Equation 2)}$$

$$\Psi=k^0[\pi DnF/RT]^{-1/2}v^{-1/2} \quad \text{(Equation 3)}$$

where F, D, and n are defined in Equation 1, R=8.314, and v represents the scan rate.

The CV of $[(NPr)_2TTz]Cl_4$ displayed $\Delta E_p$ of 53 mV and 58 mV for the $1^{st}$ and $2^{nd}$ electron reduction under 500 mV/s scan rate (FIG. 6B), respectively, confirming fast and reversible Nernst reduction processes. For Nicholson's method, $\Delta E_p$ has a limit value of 61 mV, corresponding to $\Psi$ as 20. Thus a lower limit of $k^0$ for the two reductions of $[(NPr)_2TTz]Cl_4$ was estimated using $\Psi=20$, scan rate at 500 mV/s, and corresponding diffusion constants. $k^0$ of both single-electron reductions is greater than 0.28 cm/s.

The $k^0$ for $[(NPr)_2TTz]^{4+}$ and $[(NPr)_2TTz]^{3+}$ were both greater than 0.28 cm s$^{-1}$, which indicates fast electron transfer. Regarding the high water-solubility, good electrochemical reversibility, and fast electron transfer, the $[(NPr)_2TTz]Cl_4$ is a promising anolyte candidate for AORFBs using a Cl$^-$ exchange mechanism.

Example 6: Redox Flow Battery Tests

To demonstrate the proof of concept of the two-electron storage capability of $[(NPr)_2TTz]Cl_4$, it was paired with highly water-soluble 4-trimethylammoinium-TEMPO (abbreviated as N$^{Me}$-TEMPO, 3.0 m solubility in water) for a redox flow battery test.

The flow cell was constructed from two graphite chambers, each housing a graphite felt electrode (SGL Carbon Group, Germany). Sandwiched between the chambers was a sheet of anion exchange membrane (AEM 115, 110 μm thickness, pore size<10 Å, Selemion, Japan). The cell has an active area of 10 cm$^2$ that is determined by the membrane size. On the exterior side of each graphite chamber was a copper current collector. A Masterflex® L/S® peristaltic pump (Cole-Parmer, USA) circulated the electrolyte solutions through the cell and reservoirs at 60 mL/min. Each reservoir contained 12 mL 2.0 M NaCl aqueous solution. The anode reservoir contained 0.1 M $[(NPr)_2TTz]Cl_4$, and the cathode reservoir contained 0.2 M N$^{Me}$-TEMPO. The flow battery was also tested at a higher concentration, 0.25 M $[(NPr)_2TTz]Cl_4$, and 0.5 M N$^{Me}$-TEMPO. The reservoirs were purged with N$_2$ to displace any O$_2$ in the system, and then sealed. The flow cell was galvanostatically charged to 1.8 V and discharged to 0.2 V at 25° C. using a battery tester (Land Instruments). The flow cell was operated at current densities from 40 to 100 mA/cm$^2$. The extended cycling experiment was conducted at 40 mA/cm$^2$.

The theoretical energy density of the $[(NPr)_2TTz]Cl_4$/N$^{Me}$-TEMPO AORFB was calculated using equation 4 below, where n=the number of electrons involved in the cell reaction (n=2 used for calculation), C=the concentration of active materials, F=Faraday's constant 26.8 Ah/mol, V=the cell voltage, $\mu_v$=the factor that represents the overall volumes of anolyte and catholyte.

$$\text{Energy density } (Wh/L) = nCFV/\mu_v \quad \text{(Equation 4)}$$

$$\mu_v = 1 + \frac{[\text{max concentration, less soluble electrolyte}]}{[\text{max concentration, more soluble electrolyte}]}$$

For the $[(NPr)_2TTz]Cl_4$/N$^{Me}$-TEMPO AORFB, $\mu v=1+[(NPr)_2TTz]Cl_4$N$^{Me}$-TEMPO=1+1.3 M/1.5 M=1.87. Note the effective maximum concentration (3.0 M) of N$^{Me}$-TEMPO was equivalent to 1.5 M for two electron storage. For the two-electron $[(NPr)_2TTz]Cl_4$/N$^{Me}$-TEMPO AORFB, energy density=$(2\times1.3\times26.8\times1.44)/1.87$=53.7 Wh/L.

Figure 7A:
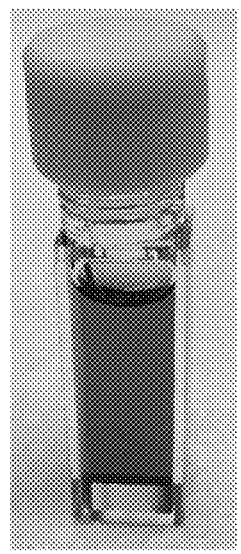
FIG. 7A and FIG. 7B show purple-colored solutions of the two-electron reduced compound [(NPr)$_2$TTz]Cl$_2$ before (FIG. 7A) and after (FIG. 7B) bubbling with air for 10 minutes to confirm the oxygen insensitivity of the reduced state (i.e., no change in color).
Figure 7B:
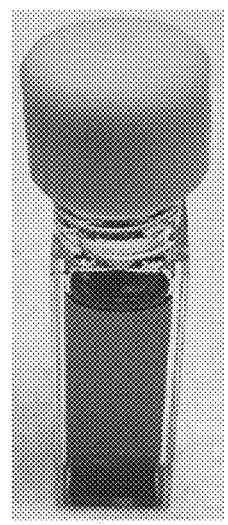

As shown in FIG. 1A, in a neutral NaCl solution, $[(NPr)_2TTz]Cl_4$ exhibited two single-electron reductions with average redox potential at 0.44 V (vs. NHE) and N$^{Me}$-TEMPO undergoes a single-electron oxidation at +1.0 V (vs. NHE). Both of these potentials are within the water splitting window (the potential gap between HER at −1.0 V and OER at +1.5 V in a neutral NaCl supporting electrolyte), which ensures their application in AORFBs. The combination of $[(NPr)_2TTz]Cl_4$ and N$^{Me}$-TEMPO enabled a 1.44 V battery voltage with a 53.7 Wh L$^{-1}$ theoretical energy density, which was higher than most of reported AORFBs. Equations in FIG. 1B give the anodic and cathodic half-cell reactions for the flow battery. In the anolyte side, the yellow $[(NPr)_2TTz]^{4+}$ was first reduced to the cation radical, $[(NPr)_2TTz]^{3+}$, at −0.38 V, and then further reduced to purple $[(NPr)_2TTz]^{2+}$ with a neutral Py$_2$TTz skeleton at −0.50 V. The two electron reduced state, $[(NPr)_2TTz]^{2+}$, was synthetically prepared and characterized by $^1$H- and $^{13}$C-NMR spectrum. Compared with the ground state, $[(NPr)_2TTz]^{4+}$, both $^1$H- and $^{13}$C-NMR signals of $[(NPr)_2TTz]^{2+}$ were upfield shifted due to its higher electron density. It is worth noting that the $[(NPr)_2TTz]^{2+}$ was oxygen insensitive (FIG. 7A and FIG. 7B), which confirmed the stabilization of the reduced state species by extending the conjugation of viologen molecules and would make the TTz-based AORFBs more tolerant. In the cathode side, N$^{Me}$-TEMPO was oxidized to the oxoammonium as the charge state and recovered to the nitroxyl radical as the discharged state through a single-electron redox process.

Figure 2A:
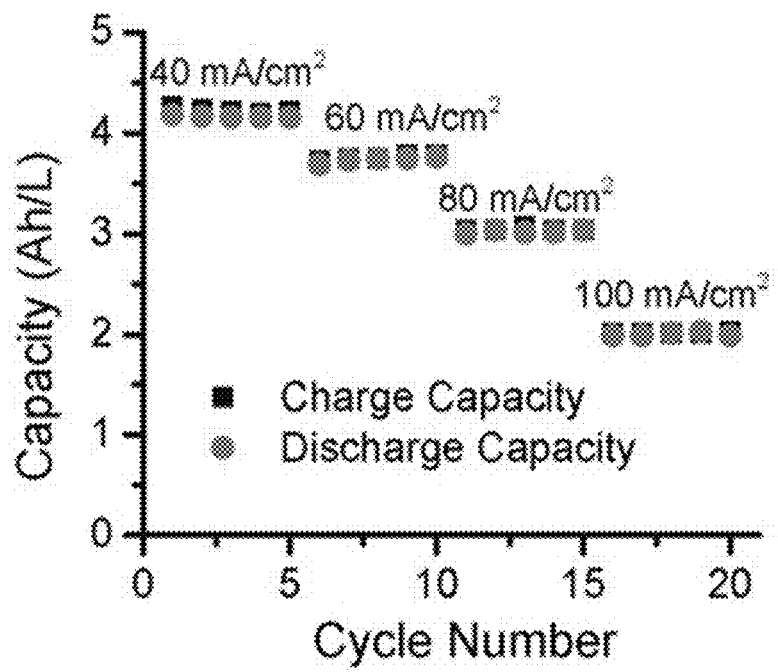
FIG. 2A, FIG. 2B, FIG. 2C, and FIG. 2D show plots of battery capacity, Coulombic efficiency, energy efficiency and voltage efficiency for a [(NPr)$_2$TTz]Cl$_4$/N$^{Me}$-TEMPO AORFB.
Figure 2B:
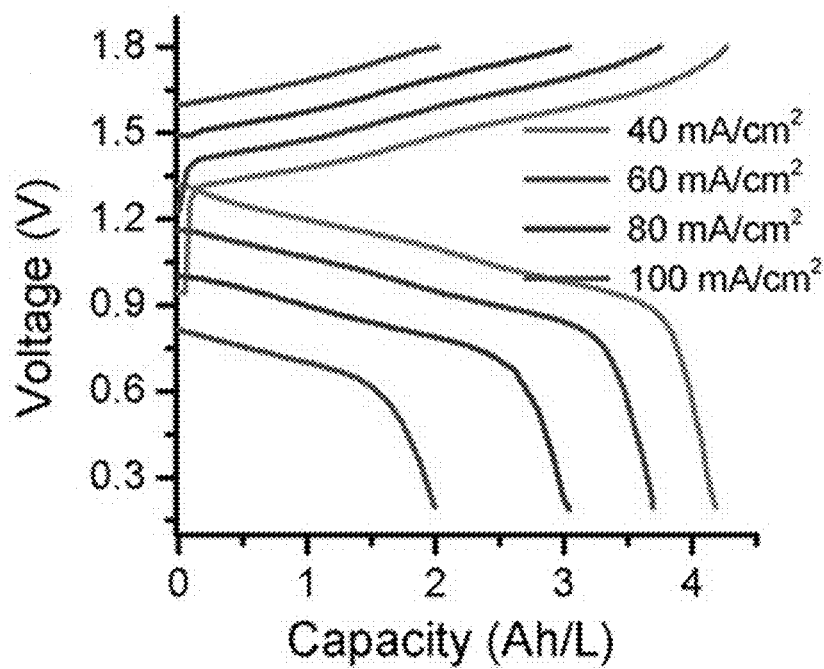
Figure 2C:
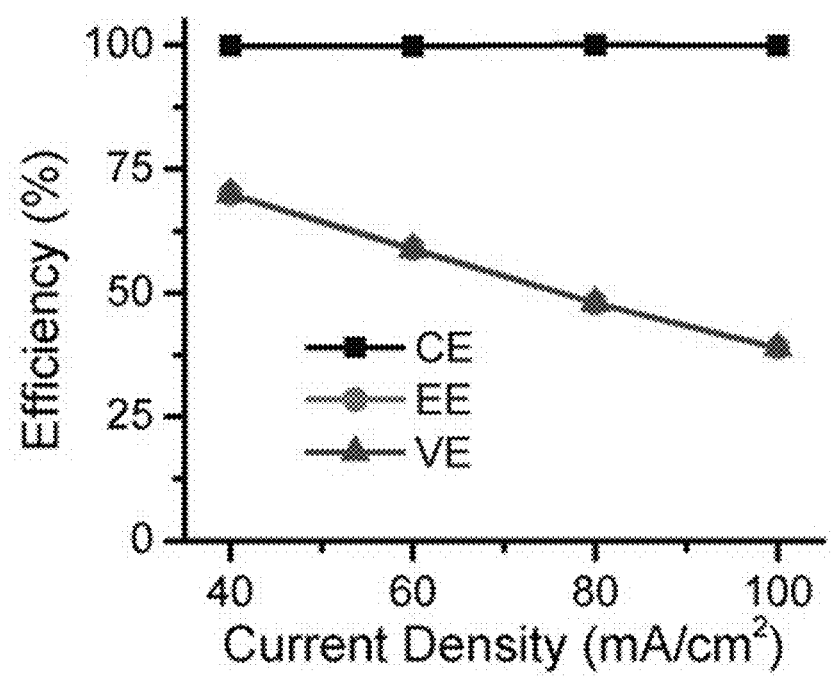
Figure 2D:
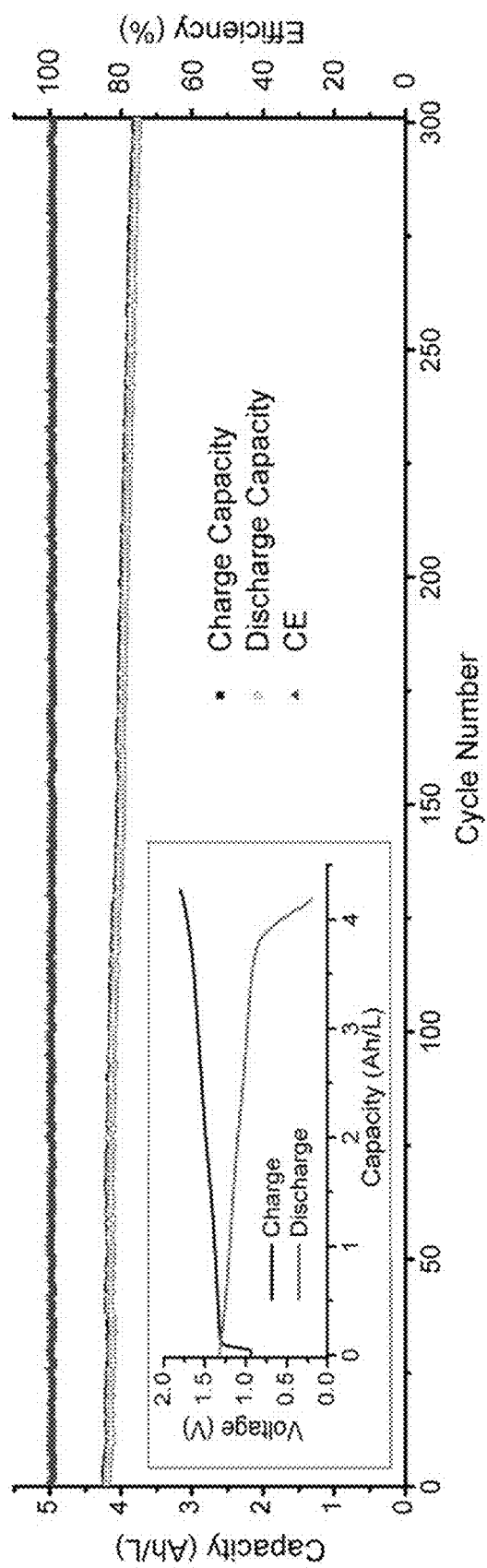

A flow battery was constructed using 0.1 M $[(NPr)_2TTz]Cl_4$ and 0.2 M N$^{Me}$-TEMPO in a 2.0 M NaCl supporting electrolyte for anolyte and catholyte (a charge capacity of 5.36 Ah L$^{-1}$ and an energy density of 3.86 Wh L$^{-1}$), respectively. Using a Selemion AMV anion-exchange membrane, the battery delivered outstanding performance as shown in FIG. 2. The current rate performance was investigated from 40 to 100 mA cm$^{-2}$ with increments of 20 mA cm' and cutoff voltages at 1.8 V for the charge process and 0.2 V for the discharge process. In five continuous cycles, stable capacity retention was observed at each current density (FIG. 2A). Upon increasing the current density from 40 to 60, 80, and 100 mA cm$^{-2}$, capacity retention gradually decreased, which was due to the increased ohmic loss and was also consistent with the increased voltage gaps of the charge/discharge curves (FIG. 2B). The Coulombic efficiency (CE) of the battery under each current density was nearly 100%. Furthermore, the battery showed reasonable energy efficiencies (EE) and voltage efficiencies (VE), for example, 70% EE and VE at 40 mA cm$^{-2}$ operational current density, and they decreased linearly with the increasing of the operational current density (FIG. 2C). The long term cycling performance of the $[(NPr)_2TTz]Cl_4$/N$^{Me}$-TEMPO AORFB was measured at 40 mA cm$^{-2}$ for 300 cycles. As shown in FIG. 2D, the flow battery delivered rather stable cycling performance, more than 90% total capacity retention after 300 cycles, equivalent to 99.97% capacity retention per cycle. It is worth noting that there are two almost merged plateaus in the charge and discharge curve, corresponding to the two single-electron redox processes (FIG. 2D, inset and FIG. 8). The CV post analysis showed no active material crossover in both anolyte and catholyte (FIG. 9).

As shown in FIG. 10, at higher concentrations of electrolytes, 0.25 M [(NPr)$_2$TTz]Cl$_4$ and 0.5 M N$^{Me}$-TEMPO as catholyte (equivalent to 0.5 m electrons), the AORFB (13.4 Ah L$^{-1}$ and 9.65 Wh L$^{-1}$) delivered similar rate performance and slightly lower energy efficiency (68.6% EE at 40 mA cm') than the 0.1 M [(NPr)$_2$TTz]Cl$_4$ and 0.2 M N$^{Me}$-TEMPO battery. Same as the previously reported viologen-based RFBs, the [(NPr)$_2$TTz]Cl$_4$N$^{Me}$-TEMPO AORFB displayed concentration dependent long-term cycling stability. Specifically, the 0.5 m electron RFB delivered 99.94% capacity retention per cycle. A mechanistic understanding of the AORFB is needed to elucidate the concentration dependent battery performance.

In summary, a π-conjugation extended viologen compound, [(NPr)$_2$TTz]Cl$_4$ was shown to function as a novel two-electron storage anolyte for total organic neutral AORFB applications. Through the rational molecular engineering, planar TTz framework was inserted into the two pyridinium moieties to adjust the electrochemistry of viologen while a highly hydrophilic 3-(trimethylaminium)propyl group was introduced to the hydrophobic Py$_2$TTz skeleton to improve solubility in water. The synthesis of [(NPr)$_2$TTz]Cl$_4$ was demonstrated through a straightforward reaction route from the commercially available reagents with a satisfactory isolation yield. [(NPr)$_2$TTz]Cl$_4$ exhibits a high solubility in water, reversible electrochemical behaviors, and fast electron transfer rate constants. Paired with the catholyte compound, N$^{Me}$-TEMPO, the [(NPr)$_2$TTz]Cl$_4$/N$^{Me}$-TEMPO flow battery enables a 1.44 V battery voltage with a theoretical energy density of 53.7 Wh L$^{-1}$. The demonstrated [(NPr)$_2$TTz]Cl$_4$/N$^{Me}$-TEMPO AORFB delivered outstanding battery performance, specifically, 70% energy efficiency and 99.97% capacity retention per cycle. The results confirmed the strategy of extending the π-conjugation of viologen molecules to obtain new redox active compounds for AORFB applications.

What is claimed is:

1. A compound of formula (I):

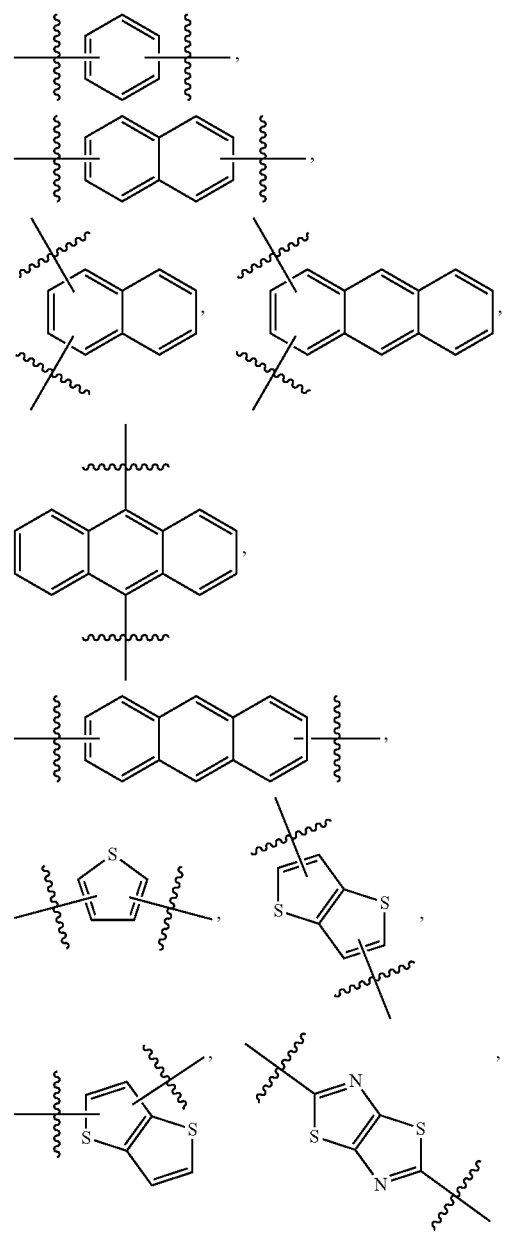

or a salt thereof, wherein:
m is 1, 2, or 3;
each A is independently selected from arylene or heteroarylene;
L$^1$ and L$^2$ are C$_1$-C$_{10}$-alkyl;
n, at each occurrence, is independently 1, 2, or 3;
R$^1$ and R$^2$ are independently selected from the group consisting of —NO$_2$, —OR$^a$, —C(O)R$^b$, —C(O)OR$^c$, —S(O)$_q$, —PO$_3$, —S(O)$_q$R$^d$, —S(O)$_q$OR$^e$, —OP(O)(OR$^f$)$_2$, —OCH$_2$, —P(O)(OR$^g$)$_2$, —CHO, —(CR$^h{}_2$)$_q$CN, —N(R$^i$)$_q$, and —P(R$^j$)$_r$;
each R$^a$, R$^b$, R$^c$, R$^d$, R$^e$, R$^f$, R$^g$, R$^h$, R$^i$ and R$^j$ are independently selected from the group consisting of hydrogen, C$_1$-C$_4$ alkyl, cycloalkyl, heterocyclyl, aryl, heteroaryl, C$_1$-C$_4$ alkyl-N(R$^k$)$_w$, C$_1$-C$_4$ alkyl-S(O)$_w$, an oxygen protecting group, and a nitrogen protecting group;

R$^k$, at each occurrence, is independently selected from the group consisting of hydrogen, alkyl, cycloalkyl, heterocyclyl, aryl, heteroaryl, an oxygen protecting group, and a nitrogen protecting group;

q, at each occurrence, is independently 2 or 3;

r, at each occurrence, is independently 2, 3, or 4; and w, at each occurrence, is independently 2 or 3;

wherein each aryl, heteroaryl, arylene, heteroarylene, cycloalkyl, and heterocyclyl is independently unsubstituted or substituted.

2. A compound of claim 1, wherein A is selected from the group consisting of:

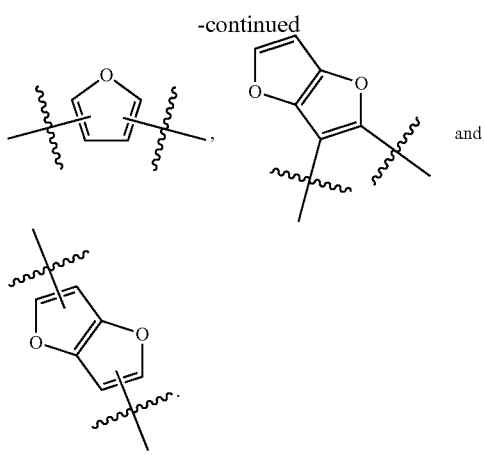

3. The compound of claim 1, wherein m is 2 and A is a five-membered or six-membered arylene or heteroarylene.

4. The compound of claim 1, wherein A is selected from the group consisting of:

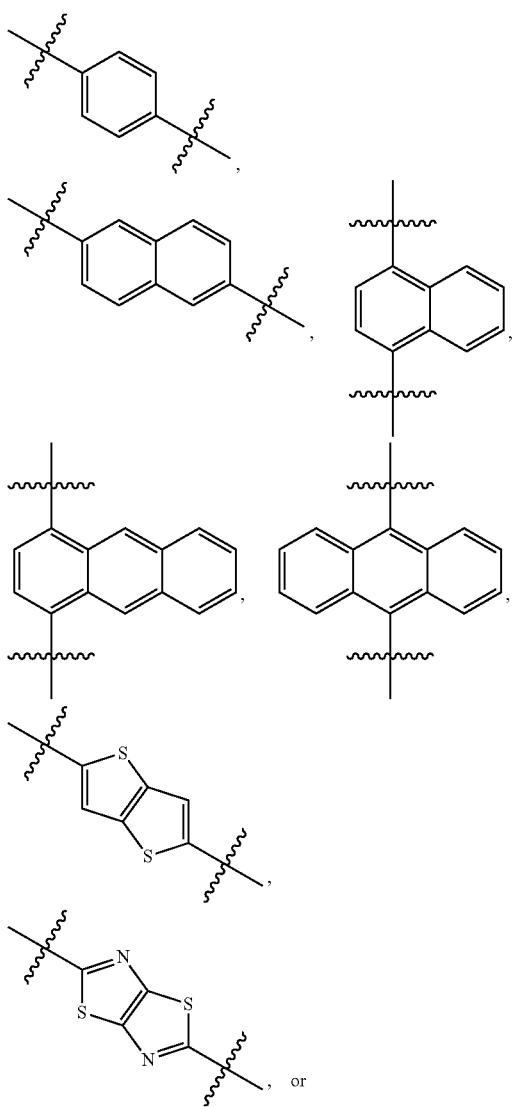

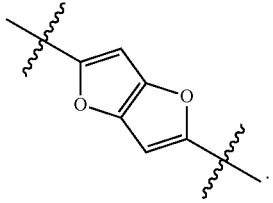

5. The compound of claim 1, wherein $R^1$ and $R^2$ are independently selected from the group consisting of —S(O)$_q$, —PO$_3$, —S(O)$_q$R$^d$, and —N(R$^i$)$_q$.

6. The compound of claim 1, wherein each R$^a$, R$^b$, R$^c$, R$^d$, R$^e$, R$^f$, R$^g$, R$^h$, R$^i$ and R$^j$ are independently selected from hydrogen and $C_1$-$C_4$ alkyl.

7. The compound of claim 1, wherein the compound is a salt of fluoride, chloride, bromide, iodide, hydroxide, sulfate, carbonate, chlorate, perchlorate, phosphate, dihydrogen phosphate, hydrogen phosphate, nitrate, nitrite, nitrile, dicyanamide, thiocyanate, bis(trifluoromethane)sulfonamide, hexafluorophosphate, tetrafluorophosphite, or a combination thereof.

8. A redox flow battery comprising:
a first redox active material; and
a second redox active material comprising a viologen or a salt thereof, wherein the viologen has formula (I):

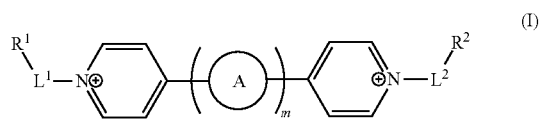

wherein:
m is 1, 2, or 3;
each A is independently selected from arylene or heteroarylene;
$L^1$ and $L^2$ are $C_1$-$C_{10}$-alkyl;
n, at each occurrence, is independently 1, 2, or 3;
$R^1$ and $R^2$ are independently selected from the group consisting of —CH$_3$, —NO$_2$, —OR$^a$, —C(O)R$^b$, —C(O)OR$^c$, —S(O)$_q$, —PO$_3$, —S(O)$_q$R$^d$, —S(O)$_q$OR$^e$, —OP(O)(OR$^f$)$_2$, —OCH$_2$, —P(O)(OR$^g$)$_2$, —CHO, —(CR$^h_2$)$_q$CN, —N(R$^i$)$_q$, and —P(R$^j$)$_r$;
each R$^a$, R$^b$, R$^c$, R$^d$, R$^e$, R$^f$, R$^g$, R$^h$, R$^i$ and R$^j$ are independently selected from the group consisting of hydrogen, $C_1$-$C_4$ alkyl, cycloalkyl, heterocyclyl, aryl, heteroaryl, $C_1$-$C_4$ alkyl-N(R$^k$)$_w$, $C_1$-$C_4$ alkyl-S(O)$_w$, an oxygen protecting group, and a nitrogen protecting group;
R$^k$, at each occurrence, is independently selected from the group consisting of hydrogen, alkyl, cycloalkyl, heterocyclyl, aryl, heteroaryl, an oxygen protecting group, and a nitrogen protecting group;
q, at each occurrence, is independently 2 or 3;
r, at each occurrence, is independently 2, 3, or 4; and
w, at each occurrence, is independently 2 or 3;
wherein each aryl, heteroaryl, arylene, heteroarylene, cycloalkyl, and heterocyclyl is independently unsubstituted or substituted.

9. A redox flow battery of claim 8, wherein A is selected from the group consisting of:

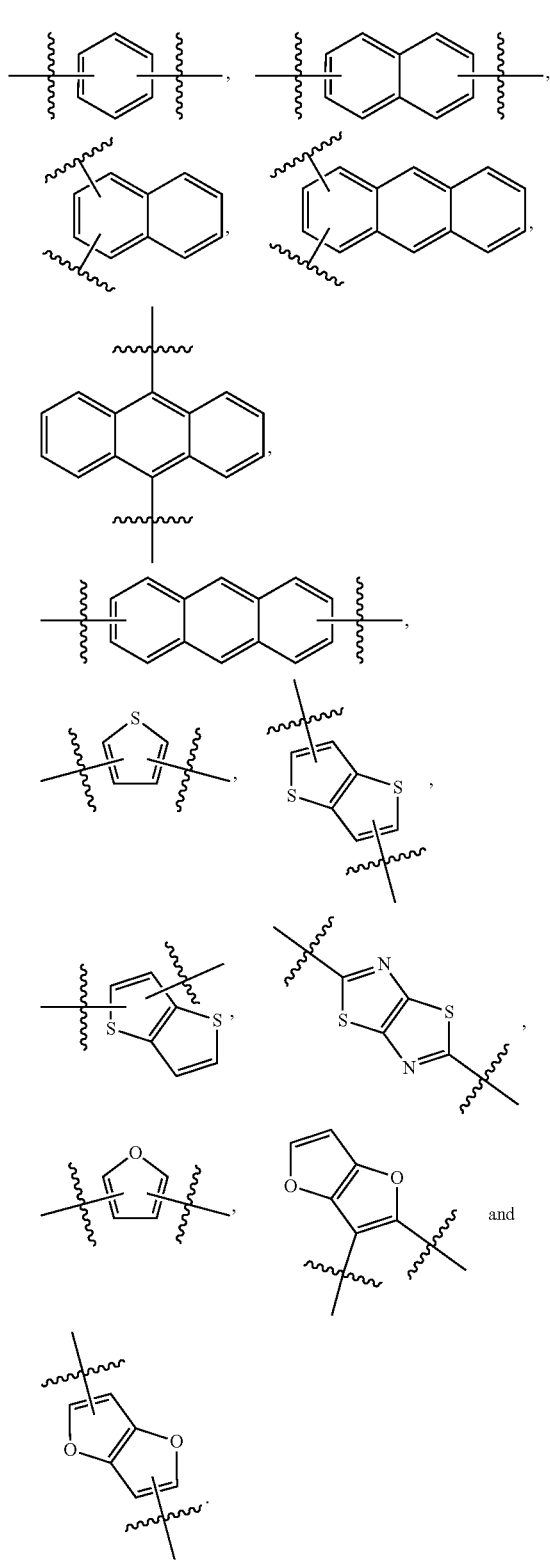

10. The redox flow battery of claim 8, wherein m is 2 and A is a five-membered or six-membered arylene or heteroarylene.

11. The redox flow battery of claim 8, wherein A is:

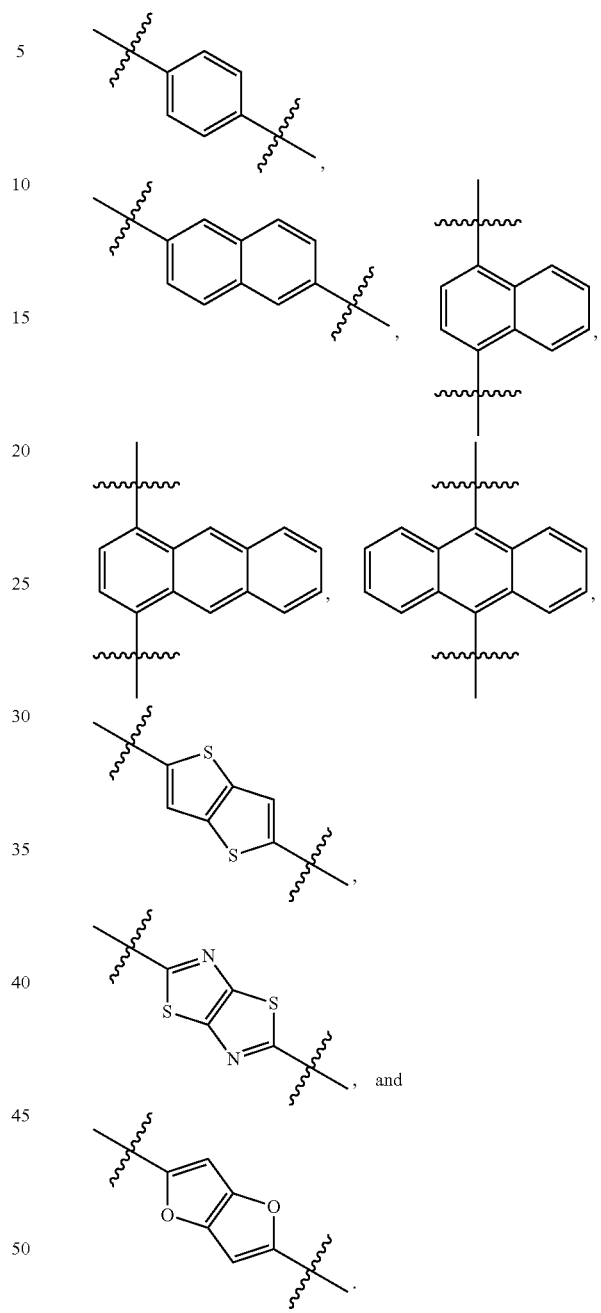

12. The redox flow battery of claim 8, wherein $R^1$ and $R^2$ are independently selected from the group consisting of —S(O)$_q$, —PO$_3$, —S(O)$_q R^d$, and —N(R$^i$)$_q$.

13. The redox flow battery of claim 8, wherein each $R^a$, $R^b$, $R^c$, $R^d$, $R^e$, $R^f$, $R^g$, $R^h$, $R^i$ and $R^j$ are independently selected from hydrogen and $C_1$-$C_4$ alkyl.

14. The redox flow battery of claim 8, wherein the compound is a salt of fluoride, chloride, bromide, iodide, hydroxide, sulfate, carbonate, chlorate, perchlorate, phosphate, dihydrogen phosphate, hydrogen phosphate, nitrate, nitride, nitrile, dicyanamide, thiocyanate, bis(trifluoromethane)sulfonamide, hexafluorophosphate, tetrafluorophosphite, or a combination thereof.

15. The redox flow battery of claim 8, wherein the first redox active material comprises $^-[Fe(CN)_6]^{3+/2+}$, $I_3^-/I^-$, $Br_2^-/Br^-$, $S_4^-/S_2$, KBr, NaBr, $NH_4Br$, KI, NaI, $NH_4I$, $FeCl_2$, $FeBr_2$, $Ce^{4+/3+}$, $Mn^{3+/2+}$, $PbO_2/PbSO_4$, quinone, a derivative of quinone, anthraquinone, a derivative of anthraquinone, $K_4[Fe(CN)_6]$, $N_4[Fe(CN)_6]$, $(NH_4)_4[Fe(CN)_6]$, $Ni(OH)_2$, $V^{5+/4+}$, (2,2,6,6-Tetramethylpiperidin-1-yl)oxyl (TEMPO), a derivative of TEMPO, or a combination thereof.

16. The redox flow battery of claim 15, wherein the derivative of TEMPO is selected from the group consisting of 4-trimethylammonium-(2,2,6,6-Tetramethylpiperidin-1-yl)oxy (4-$N^{Me}$-TEMPO), 4-dimethyl(propyl-3-N,N,N,-trimethylammonium)-(2,2,6,6-Tetramethylpiperidin-1-yl)oxy ((4-$N^{NPr}$-TEMPO), 4-hyoxyl-ammonium-(2,2,6,6-Tetramethylpiperidin-1-yl)oxy (4-OHTEMPO), 4-sulfonate-(2,2,6,6-Tetramethylpiperidin-1-yl)oxy (4-$SO_3$-TEMPO), 4-amino-(2,2,6,6-Tetramethylpiperidin-1-yl)oxy (4-$NH_2$-TEMPO), N,N,N,2,2,6,6-heptamethylpiperidinyloxy-4-ammonium chloride ($N^{Me}$-TEMPO), and a combination thereof.

17. The redox flow battery of claim 8, further comprising:
a first aqueous electrolyte;
a second aqueous electrolyte; and
a separator between the first and second aqueous electrolytes.

18. The redox flow battery of claim 17, wherein the second redox active material is present in the second aqueous electrolyte at a concentration of ≥0.1 M.

19. The redox flow battery claim 17, further comprising a first electrode in contact with the first aqueous electrolyte and a second electrode in contact with the second aqueous electrolyte.

20. The redox flow battery of claim 17, wherein the separator is a porous separator.

21. The redox flow battery of claim 17, wherein the separator is an anion exchange membrane or a cation exchange membrane.

22. The redox flow battery of claim 17, wherein the first and second aqueous electrolytes each independently comprise a salt having the formula (IV):

A-B  (II), wherein:
A is $Na^+$, $K^+$, $Li^+$, $NR^m_4{}^+$, pyridinium, pyrrolidium, or imidazolium;
$R^m$ is independently selected from the group consisting of hydrogen, alkyl, cycloalkyl, heterocyclyl, aryl, and heteroaryl; and
B is halide anion, $SO_4^{2-}$, $OH^-$, $CO_3^{2-}$, $ClO_4^-$, $H_2PO_4^-$, $HPO_4^{2-}$, $PO_4^{3-}$, $NO_3^-$, $N_3^-$, $CN^-$, $N(CN)_2^-$, or $SCN^-$.

23. The redox flow battery of claim 17, wherein the first and second electrolytes each independently comprise NaCl, KCl, or $NH_4Cl$.

24. The redox flow battery of claim 17, wherein the first and second aqueous electrolytes each independently comprise between about 0.5 M to about 5 M NaCl, KCl, or $NH_4Cl$.

25. The redox flow battery of claim 17, further comprising:
a first circulation loop comprising a first storage tank containing the first aqueous electrolyte, piping for transporting the first aqueous electrolyte, a chamber in which the first electrode is in contact with the first aqueous electrolyte, and a pump to circulate the first aqueous electrolyte through the first circulation loop;
a second circulation loop comprising a second storage tank containing the second aqueous electrolyte, piping for transporting the second aqueous electrolyte, a chamber in which the second electrode is in contact with the second aqueous electrolyte, and a pump to circulate the second aqueous electrolyte through the second circulation loop; and
control hardware and software.

26. A method of storing energy, comprising applying a potential difference across the first and second electrode of the redox flow battery of claim 8, wherein the first redox active material is oxidized.

27. A method of releasing energy, comprising applying a potential difference across the first and second electrode of the redox flow battery of claim 8, wherein the first redox active material is reduced.

* * * * *